United States Patent
Xu et al.

(10) Patent No.: US 9,156,801 B2
(45) Date of Patent: Oct. 13, 2015

(54) 2-SUBSTITUTED OLEANOLIC ACID DERIVATIVE, METHOD PREPARING FOR SAME, AND APPLICATION THEREOF

(71) Applicant: HANGZHOU BENSHENG PHARMACEUTICAL CO., LTD., Zhejiang (CN)

(72) Inventors: Rongzhen Xu, Zhejiang (CN); Frank Rong, Zhejiang (CN); Hongxi Lai, Fujian (CN); Fuwen Xie, Fujian (CN)

(73) Assignee: Hangzhou Bensheng Pharmaceutical Co., Ltd., Zhejiang (CN)

( * ) Notice: Subject to any disclaimer, the term of this patent is extended or adjusted under 35 U.S.C. 154(b) by 0 days.

(21) Appl. No.: 14/362,017

(22) PCT Filed: Nov. 30, 2012

(86) PCT No.: PCT/CN2012/085652
§ 371 (c)(1),
(2) Date: May 30, 2014

(87) PCT Pub. No.: WO2013/079018
PCT Pub. Date: Jun. 6, 2013

(65) Prior Publication Data
US 2014/0343064 A1    Nov. 20, 2014

(30) Foreign Application Priority Data
Dec. 1, 2011    (WO) ................ PCT/CN2011/083288

(51) Int. Cl.
| | | |
|---|---|---|
| *A61K 31/21* | (2006.01) |
| *A61K 31/44* | (2006.01) |
| *A61K 31/497* | (2006.01) |
| *A61K 31/535* | (2006.01) |
| *C07C 69/74* | (2006.01) |
| *C07D 211/68* | (2006.01) |
| *C07D 265/30* | (2006.01) |
| *C07D 241/04* | (2006.01) |
| *C07D 487/00* | (2006.01) |
| *C07D 295/13* | (2006.01) |
| *C07J 63/00* | (2006.01) |
| *C07C 235/84* | (2006.01) |
| *C07D 213/40* | (2006.01) |

(52) U.S. Cl.
CPC ............ *C07D 295/13* (2013.01); *C07C 235/84* (2013.01); *C07D 213/40* (2013.01); *C07J 63/00* (2013.01); *C07J 63/008* (2013.01)

(58) Field of Classification Search
CPC .................................... C07J 63/006
USPC .......... 514/237.8, 252.12, 357, 510; 544/154, 544/358; 546/285; 548/418; 560/116
See application file for complete search history.

(56) References Cited

FOREIGN PATENT DOCUMENTS

| | | |
|---|---|---|
| CN | 1874765 A | 12/2006 |
| CN | 101974059 A | 2/2011 |
| JP | 4187658 A | 7/1992 |
| WO | 2009129545 A1 | 10/2009 |
| WO | 2009146216 A2 | 12/2009 |

OTHER PUBLICATIONS

Sun et al. (2006) "Structure-activity relationships of oleanane—and ursane—type triterpenoids," Botanical Studies. 47:339-368.
Honda et al. (1999) "Novel Synthetic Oleanane Triterpenoids: A Series of Highly Active Inhibitors of Nitric Oxide Production in Mouse Macrophages," Bioorganic & Medicinal Chemistry Letters. 9:3429-3434.
Honda et al. (1998) "Design and Synthesis of 2-Cyano-3,12-Dioxoolean-1,9-Dien-28-Oic Acid, A Novel and Highly Active Inhibitor of Nitric Oxide Production in Mouse Macrophages," Bioorganic & Medicinal Chemistry Letters. 8:2711-2714.
Kaur et al. (2011) "A Comparative Study of Proapoptotic Potential of Cyano Analogues of Boswellic Acid and 11-Keto-Boswellic Acid," European Journal of Medicinal Chemistry. 46:1356-1366.
Li et al. (2012) "Synthesis and Biological Evaluation of Oleanolic Acid Derivatives as Novel Inhibitors of Protein Tyrosine Phosphate 1B," Heterocycles. 85:1117-1139.
Supplementary European Search Report issued in EP 12852723 on Jul. 15, 2015 (9 pages).

*Primary Examiner* — Barbara P Badio
(74) *Attorney, Agent, or Firm* — Lathrop & Gage LLP; Brian C. Trinque

(57) ABSTRACT

The present invention belongs to the field of natural medicine and pharmaceutical chemistry, and specifically relates to novel 2-substituted oleanolic acid derivatives of formula (I) or a pharmaceutically acceptable salt thereof, to a process for the preparation of these compounds, compositions containing such compounds and their use in preparing antineoplastic medicaments.

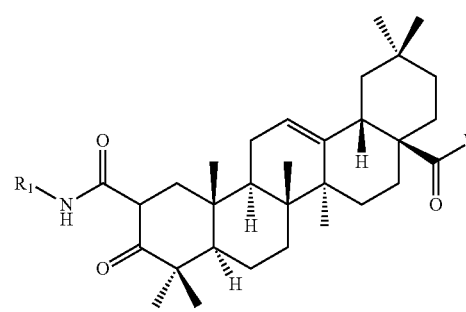

13 Claims, No Drawings

2-SUBSTITUTED OLEANOLIC ACID DERIVATIVE, METHOD PREPARING FOR SAME, AND APPLICATION THEREOF

RELATED APPLICATIONS

This application is a 35 U.S.C. §371 filing of International Application No. PCT/CN2012/085652, filed Nov. 30, 2012, which claims priority to Chinese PCT No. PCT/CN2011/083288, filed Dec. 1, 2011, each of which is incorporated herein by reference in its entirety.

TECHNICAL FIELD

The present invention belongs to the field of natural medicine and pharmaceutical chemistry, and relates to novel oleanolic acid derivatives, in particular 2-substituted oleanolic acid derivatives, to a process for the preparation of these compounds, compositions containing such compounds and their use in preparing antineoplastic medicaments.

BACKGROUND OF THE INVENTION

Oleanolic acid (OA), also known as caryophyllin, is a type of pentacyclic triterpenoids. It is extracted from the leaves and fruits of Oleaceae, Gentianaceae, Rubiaceae, Amaranthaceae, and the like, and is mainly present in free form and (or) in combination with saccharides. Many scientists, domestic and overseas, have conducted extensive research on pentacyclic triterpenoids. According to the literature, oleanolic acid and derivatives or analogs thereof exhibit a variety of biological activities, such as anti-inflammation, antitumor, antivirus, immunoregulation, inhibition of platelet aggregation, hypolipidemic, liver protection, kidney protection, anti-HIV, etc. (LI, Yingxia et al., An oleanolic acid-lactose conjugate, the preparation process and use thereof, [P] CN 1414012 A.2003; ZHANG, Yihua et al., An oleanolic acid derivative, the preparation process and use thereof, [P] CN 102070697 A.2011; Lin, Z. H.; Zhang, Y.; Zhang, Y. N.; Shen, H.; Hu, L. H.; Jiang, H. L.; Shen, X. Oleanolic acid derivative NPLG441 potently stimulates glucose transport in 3T3-L1 adipocytes via a multi-target mechanism. Biochemical Pharmacology. 2008. 76:1251-1262; Chen, J.; Gong, Y. C.; Liu, J.; Hua, W. Y.; Zhang, L. Y.; Sun, H. B. Synthesis and biological evaluation of novel pyrazolo[4,3-b]oleanane derivatives as inhibitors of glycogen phosphorylase. Chemistry & Biodiversity. 2008. 5: 1304-1312).

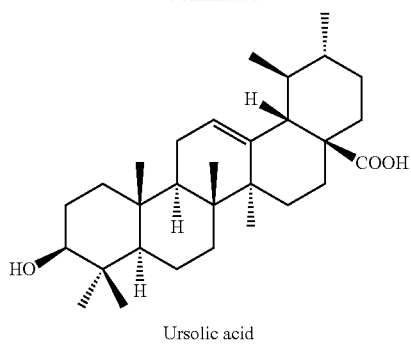

Ursolic acid

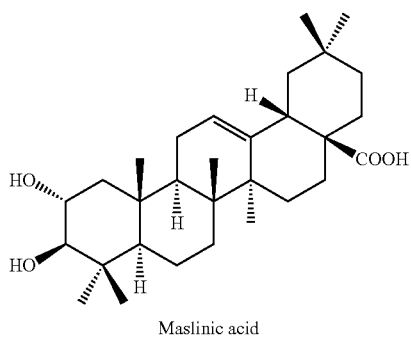

Maslinic acid

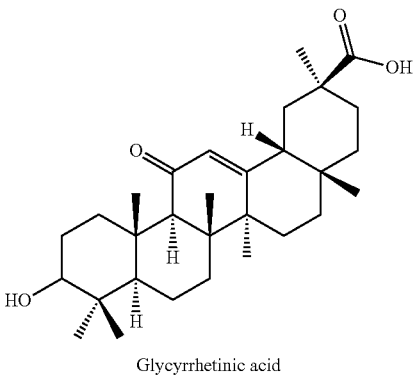

Glycyrrhetinic acid

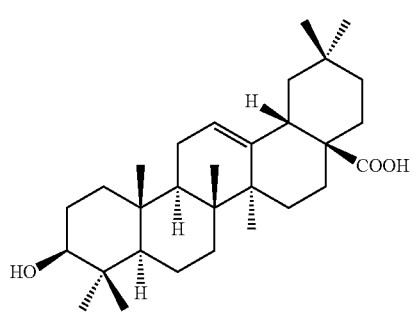

Oleanolic acid

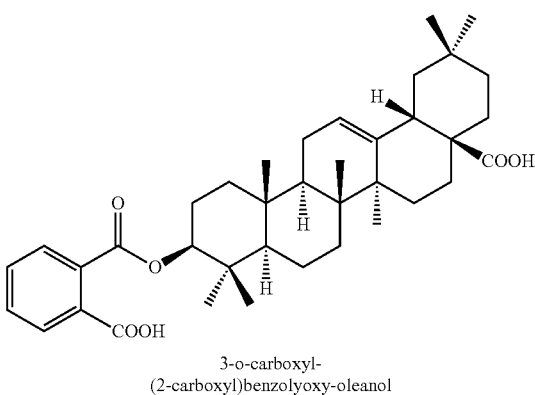

3-o-carboxyl-(2-carboxyl)benzolyoxy-oleanol

-continued

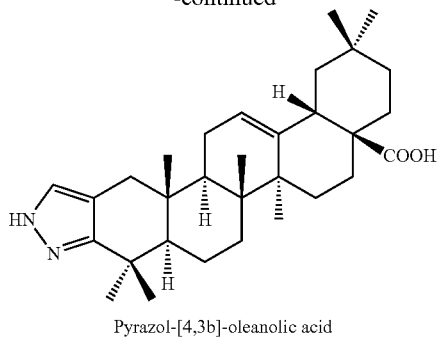

Pyrazol-[4,3b]-oleanolic acid

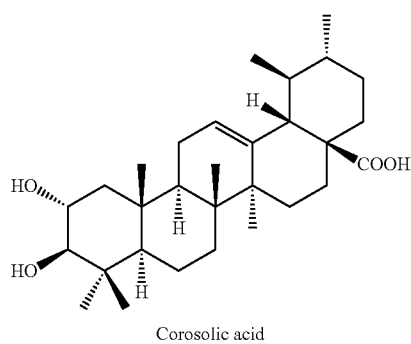

Corosolic acid

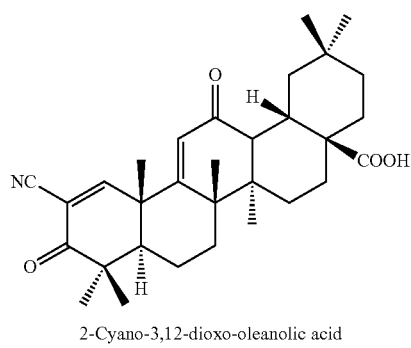

2-Cyano-3,12-dioxo-oleanolic acid

Oleanolic Acid, the Derivatives and Analogs Thereof

Nowadays, malignant tumor is the most serious common disease and poses threats to human health. The development of anti-tumor drugs is an important research topic of modern medicine. It has become a focus of the anti-tumor research domestic and overseas to search for drugs with high efficacy and low toxicity from Chinese herbal plants. Oleanolic acid, with low toxicity and having abundant resource in Chinese herbal medicine, is a very promising anti-tumor drug and has attracted widespread attention.

Recent years witnessed the literature report of oleanolic acid for its function against human lung cancer cell proliferation, and its ability of anti-invasion and inducing cell apoptosis. Researchers observed the effects of oleanolic acid on the invasion ability of PGCL3 cells through cell proliferation inhibition assay, soft agar colony formation assay, and the like. Results showed that oleanolic acid could reduce proliferation of PGCL3 cells in a dose-dependent correlation, had the effects of anti-proliferation and anti-invasion of PGCL3 human lung cancer cells, and had the effect of inducing apoptosis of PGCL3 cells. Its anti-invasion effect lies not only in the blocking of a particular step of the invasion, but the inhibition of each basic step of the invasion. In addition, researchers explored the effect of oleanolic acid on A549 cells and the possible mechanism thereof, and the results showed that oleanolic acid was capable of a concentration-dependent induction of apoptosis of human lung adenocarcinoma cells. (ZHANG Dongfang et al., Study on proliferation inhibition and anti-invasion and apoptotic induction of oleanolic acid in human lung cancer cell line, 2003, 30 (3): 081-381; WEI Xiaohong et al., Apoptosis induced by oleanolic acid and its relation to intracellular calcium of human lung adenoma A549 cells, Journal of Tongji University (Medical Science), 2009, 30 (5): 19-23.)

Literature reported that researchers studied the inhibition of ovarian cancer cell line IGROV1 and human breast cancer cell line MDA-MB-231 by oleanolic acid via detecting the activity of tumor cells through inhibition tests of cell proliferation and MTT method. The results showed that oleanolic acid could reduce the proliferation ability of IGROV1 and MDA-MB-231 cells in a dose-dependent correlation, which indicated that oleanolic acid had inhibitory activity against these two malignant tumor cell lines. (WU, Linwei et al, Inhibiting Effect of Oleanolic Acid on Ovarian Carcinomas IGROV1 and Breast Cancer Cell Line MDA-MB-231, Chinese Journal of Applied and Environmental Biology, 2010, 16(2): 202-204.)

Recently, LIN Xiukun et al. reported the excellent anti-pancreatic cancer effects of oleanolic acid and pharmaceutical preparations thereof, which was represented by the obvious inhibitory activity on human pancreatic cancer cells in vitro and the significant antitumor activity on nude mice with transplanted tumor of these tumor cells. In addition, LIN Xiukun et al. also studied the inhibitory effect of oleanolic acid on cervical cancer. The results showed that oleanolic acid and pharmaceutical preparations thereof had obvious in vitro inhibitory activity on human cervical carcinoma cells and also had significant antitumor activity on transplanted tumor in nude mice of these tumor cells. (LIN Xiukun et al., Anti-pancreatic carcinoma effects of oleanolic acid and pharmaceutical preparations thereof, [P] CN 102151275 A.2011; LIN Xiukun et al., Anti-cervical cancer effects of oleanolic acid and pharmaceutical preparations thereof, [P] CN 102133219 A.2011.)

Oleanolic acid is widely applied in clinics due to its various pharmacological activities and low toxicity, but this type of drug has low bioavailability in a human body. Therefore, oleanolic acid derivatives with high efficiency and low toxicity have good prospects in industry. According to the present invention, oleanolic acid is modified on its 2-position by substitution and functional groups are introduced to improve its biological activity and bioavailability. Up to now, reports on the method of the present invention and 2-substituted oleanolic acid derivatives have not yet been seen in the literature.

SUMMARY OF THE INVENTION

One object of the present invention is to provide novel 2-substituted oleanolic acid derivatives of formula (I),

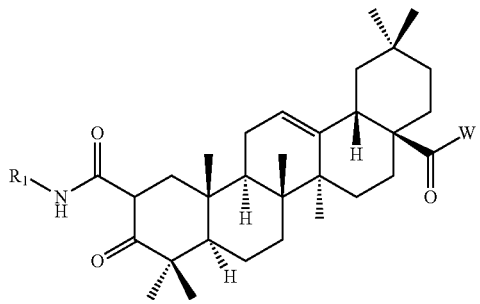

wherein $R_1$ is selected from the group consisting of H, optionally substituted $C_1$-$C_{18}$ alkyl, optionally substituted $C_2$-$C_{18}$ alkenyl or alkynyl, optionally substituted $C_3$-$C_7$ cycloalkyl or cycloalkenyl, and optionally substituted aryl, and optionally substituted heterocyclyl or heteroaryl, each of which is optionally substituted with a substituent selected from the group consisting of halogen, nitro, cyano, amino, hydroxyl, thiol, carboxyl, $C_1$-$C_6$ alkylamino, bi($C_1$-$C_6$ alkyl)amino, $C_1$-$C_6$ alkoxy, and $C_1$-$C_6$ alkylthio, said $C_3$-$C_7$ cycloalkyl or cycloalkenyl, aryl, heterocyclyl or heteroaryl further being optionally substituted with $C_1$-$C_6$ alkyl, or $R_1$ being $C_1$-$C_6$ alkyl substituted with a group selected from said $C_3$-$C_7$ cycloalkyl or cycloalkenyl, aryl, heterocyclyl or heteroaryl; and wherein W is selected from the group consisting of hydroxyl, amino, $C_1$-$C_6$ alkylamino, bi($C_1$-$C_6$ alkyl)amino, $C_1$-$C_6$ alkoxy, and $C_1$-$C_6$ alkylthio;

or a pharmaceutically acceptable salt thereof.

The second object of the present invention is to provide a process for preparing the 2-substituted oleanolic acid derivatives of formula (I) of the present invention,

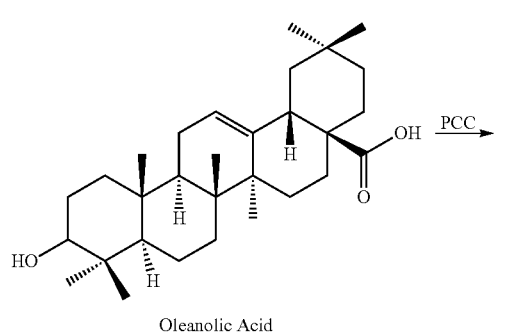

Oleanolic Acid

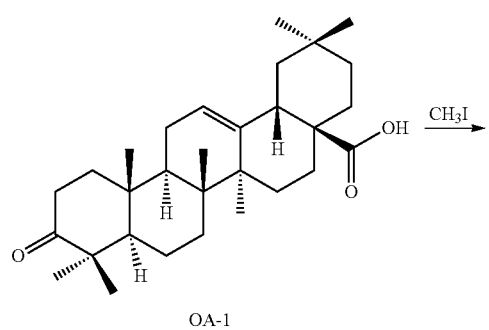

OA-1

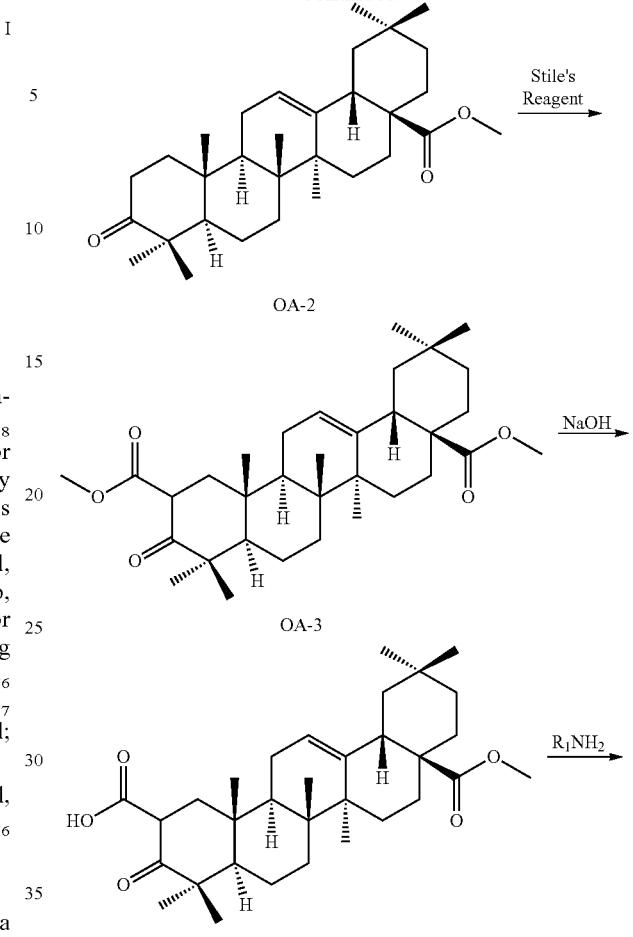

wherein oleanolic acid (OA) is subjected to oxidation to produce a ketone intermediate of oleanolic acid (OA-1); said intermediate is subjected to esterification to produce a methyl ester (ketone) intermediate of oleanolic acid (OA-2); this intermediate reacts with Stile's Reagent, resulting in the introduction of a methoxycarbonyl group to the ortho-position of the ketone carbonyl to produce a diester intermediate of oleanolic acid (OA-3); said diester intermediate is hydrolyzed to produce a monocarboxyl intermediate of oleanolic acid (OA-4); alternatively, the introduction of the methoxycarbonyl group and the hydrolysis can also be completed in a one-pot reaction to produce the monocarboxyl intermediate of oleanolic acid (OA-4); said monocarboxyl intermediate is subjected to an amido bond formation reaction with an organic amine to produce the 2-substituted oleanolic acid derivative (I), wherein $R_1$ and W are as defined in the formula (I) above.

The third object of the present invention is to provide a pharmaceutical composition comprising the compound of the present invention, said pharmaceutical composition comprising at least one compound of the present invention and optionally a pharmaceutically acceptable excipient.

The fourth object of the present invention is to provide the use of the compound of the present invention or the pharmaceutical composition comprising the same in the manufacture of a medicament, in particular an antitumor medicament. Correspondingly, the present invention provides a method for treating a subject suffering from tumor, comprising administrating to the subject in need thereof an effective amount of at least one compound of the present invention. Said tumor is particularly selected from leukemia, multiple myeloma, lymphoma, liver cancer, gastric cancer, breast cancer, cholangiocellular carcinoma, pancreatic cancer, lung cancer, colorectal cancer, osteosarcoma, melanoma, human cervical cancer, glioma, nasopharyngeal carcinoma, laryngeal carcinoma, esophageal cancer, middle ear tumor, prostate cancer, and the like.

The present invention also relates to the compounds of the present invention used for treating a tumor.

SPECIFIC EMBODIMENTS OF THE INVENTION

The present invention relates to a novel 2-substituted oleanolic acid derivative of formula (I),

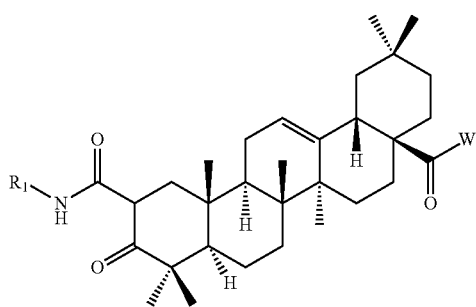

I wherein $R_1$ is selected from the group consisting of H, optionally substituted $C_1$-$C_{18}$ alkyl, optionally substituted $C_2$-$C_{18}$ alkenyl or alkynyl, optionally substituted $C_3$-$C_7$ cycloalkyl or cycloalkenyl, optionally substituted aryl, optionally substituted heterocyclyl or heteroaryl, each of which is optionally substituted with a substituent selected from the group consisting of halogen, nitro, cyano, amino, hydroxyl, thiol, carboxyl, $C_1$-$C_6$ alkylamino, bi($C_1$-$C_6$ alkyl)amino, $C_1$-$C_6$ alkoxy, and $C_1$-$C_6$ alkylthio, said $C_3$-$C_7$ cycloalkyl or cycloalkenyl, aryl, heterocyclyl or heteroaryl further being optionally substituted with $C_1$-$C_6$ alkyl, or $R_1$ being $C_1$-$C_6$ alkyl substituted with a group selected from the group consisting of said $C_3$-$C_7$ cycloalkyl or cycloalkenyl, aryl, heterocyclyl and heteroaryl; and
wherein W is selected from the group consisting of hydroxyl, amino, $C_1$-$C_6$ alkylamino, bi($C_1$-$C_6$ alkyl)amino, $C_1$-$C_6$ alkoxy, and $C_1$-$C_6$ alkylthio;
or a pharmaceutically acceptable salt thereof.

According to a preferred embodiment of the present invention, $R_1$ is $C_4$-$C_8$ alkyl, cycloalkyl-$C_1$-$C_6$ alkyl, heterocyclyl-$C_1$-$C_6$ alkyl, $C_1$-$C_6$ alkylamino-$C_1$-$C_6$ alkyl, bi($C_1$-$C_6$ alkyl)-$C_1$-$C_6$ alkyl, heteroaryl-$C_1$-$C_6$ alkyl, $C_1$-$C_6$ alkoxy-$C_1$-$C_6$ alkyl, said cycloalkyl, heterocyclyl and heteroaryl being optionally substituted with halogen, hydroxyl, $C_1$-$C_6$ alkoxy, $C_1$-$C_6$ alkyl, amino, $C_1$-$C_6$ alkylamino, or bi($C_1$-$C_6$ alkyl) amino.

According to another preferred embodiment of the present invention, $R_1$ is $C_4$-$C_6$ alkyl, cycloalkyl-$C_1$-$C_4$ alkyl, heterocyclyl-$C_1$-$C_4$ alkyl, $C_1$-$C_6$ alkylamino-$C_1$-$C_4$ alkyl, bi($C_1$-$C_6$ alkyl)-$C_1$-$C_4$ alkyl, heteroaryl-$C_1$-$C_4$ alkyl, $C_1$-$C_6$ alkoxy-$C_1$-$C_4$ alkyl, said cycloalkyl, heterocyclyl and heteroaryl being optionally substituted with halogen, hydroxyl, $C_1$-$C_6$ alkoxy, $C_1$-$C_6$ alkyl, amino, $C_1$-$C_6$ alkylamino, bi($C_1$-$C_6$ alkyl) amino.

According to a preferred embodiment of the present invention, the heterocyclyl is a saturated heterocyclyl.

According to another preferred embodiment of the present invention, the heterocyclyl comprises a nitrogen atom as a ring member and as a connection point.

According to a particularly preferred embodiment of the present invention, the heterocyclyl is pyrrolidin-1-yl, piperidin-1-yl, piperazin-1-yl, 4-methylpiperazin-1-yl, morpholino, oxazolidinyl, imidazolidinyl, or isooxazolidinyl.

According to another particularly preferred embodiment of the present invention, W is hydroxyl or $C_1$-$C_6$ alkoxy.

According to a preferred embodiment of the present invention, the heteroaryl is pyridyl, furanyl, thienyl, pyrrolyl, pyranyl, or imidazolyl.

Some of the preferred 2-substituted oleanolic acid derivatives according to the present invention are shown below. These examples are only intended to further illustrate the present invention but not to make any restriction to the scope of the present invention.

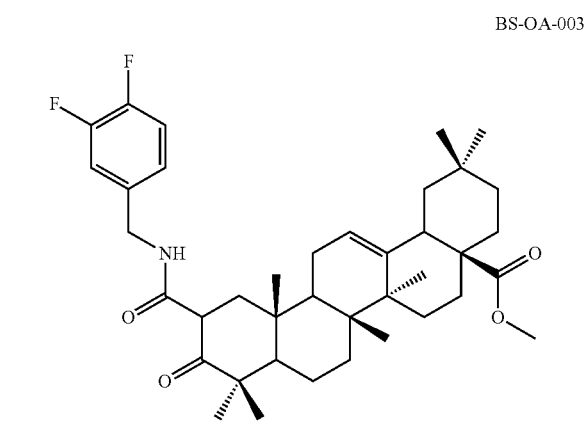

BS-OA-003

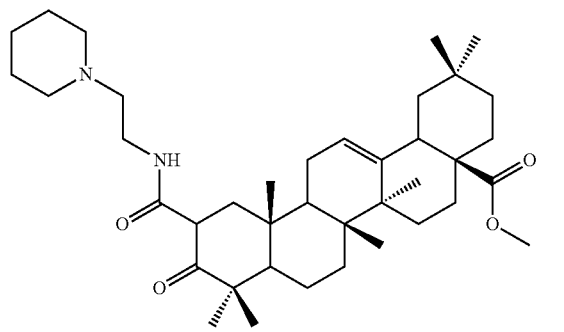

BS-OA-004

-continued
BS-OA-005
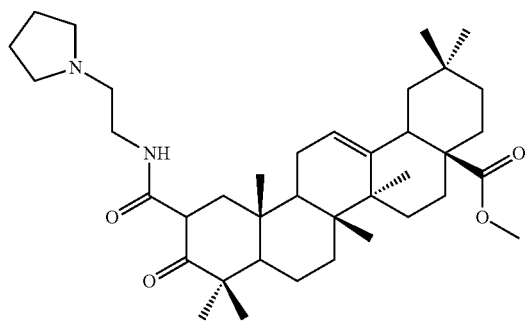
BS-OA-008
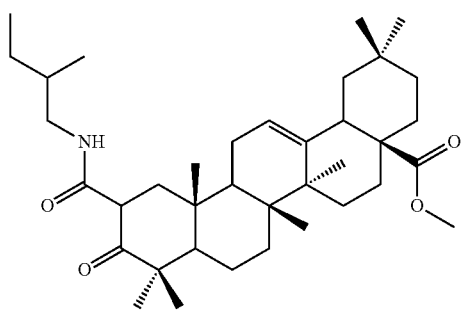
BS-OA-011
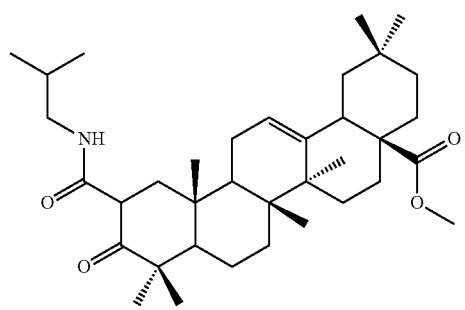
BS-OA-012
-continued
BS-OA-016
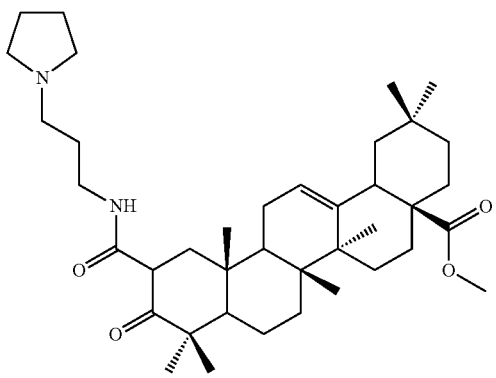
BS-OA-017
BS-OA-021
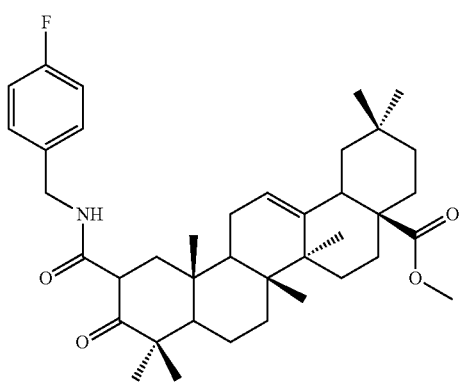
BS-OA-024
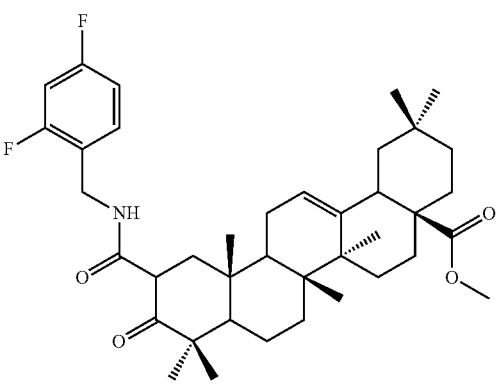

-continued
BS-OA-027
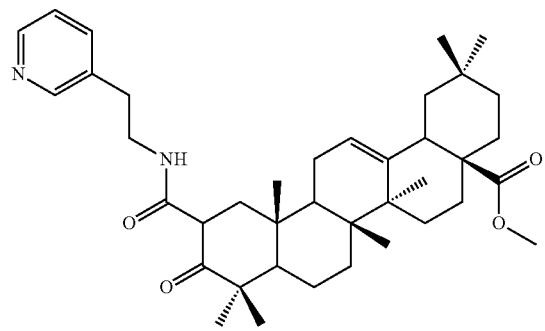
BS-OA-028
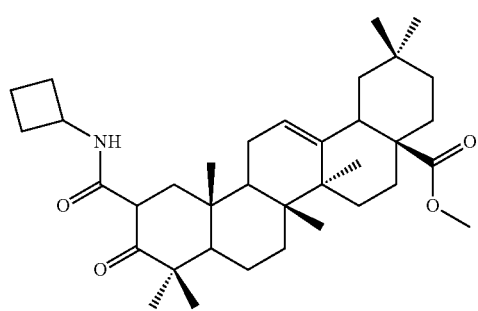
BS-OA-031
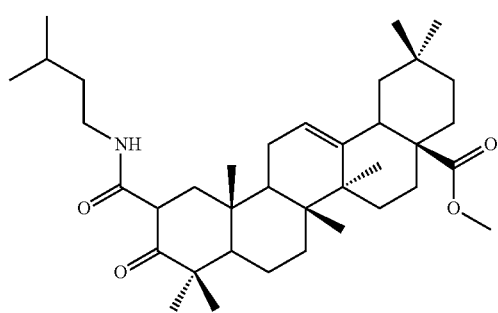
BS-OA-032
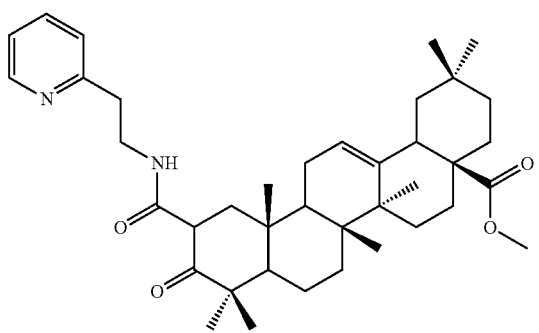
-continued
BS-OA-033
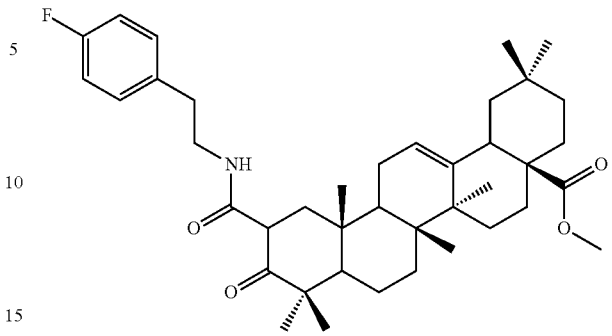
BS-OA-034
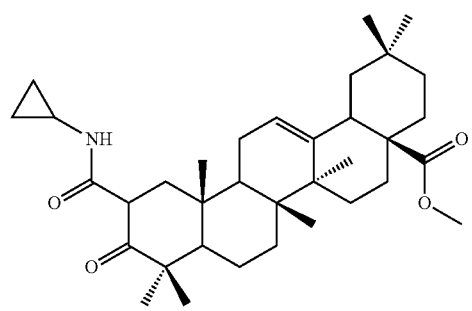
BS-OA-035
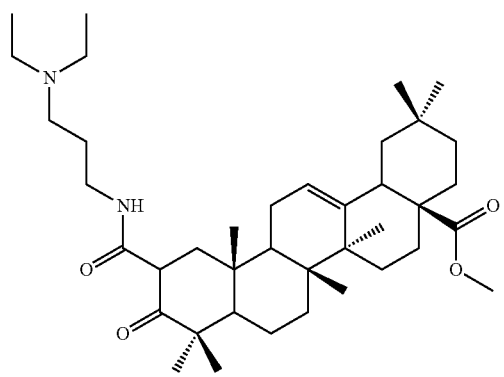
BS-OA-037
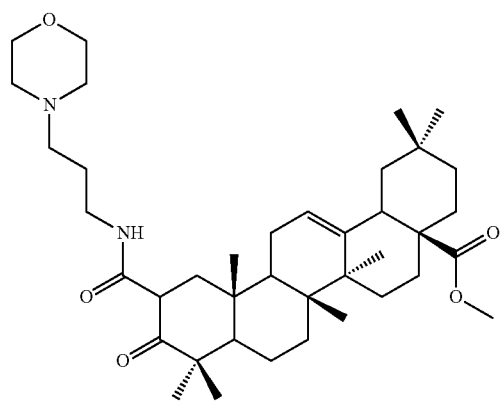

BS-OA-038
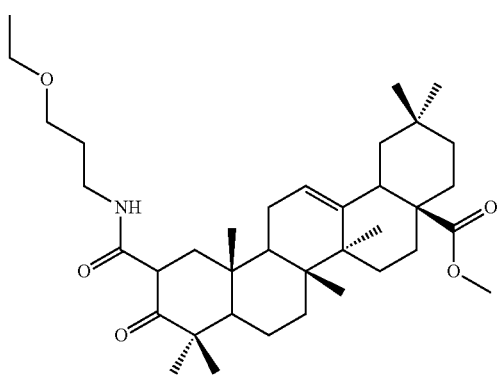
BS-OA-042
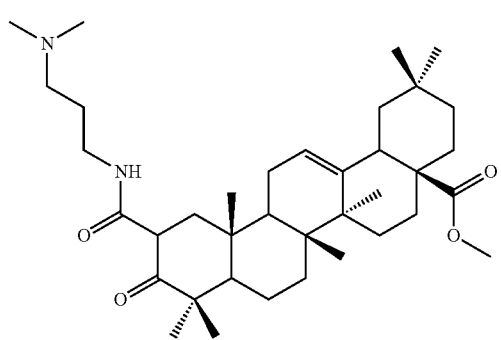
BS-OA-044
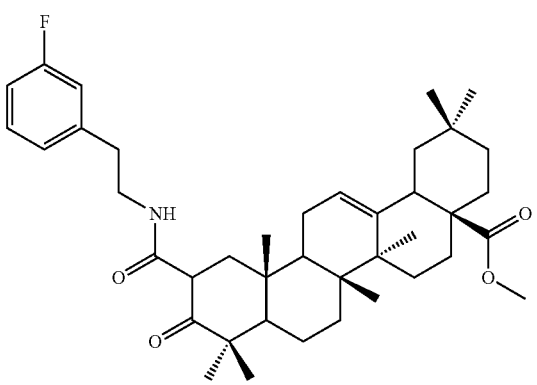
BS-OA-046
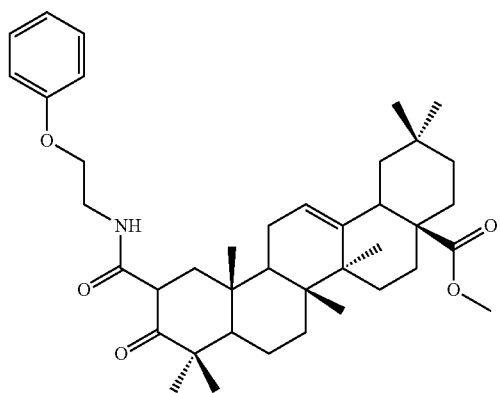
BS-OA-048
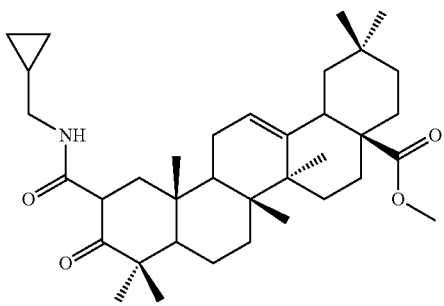
BS-OA-052
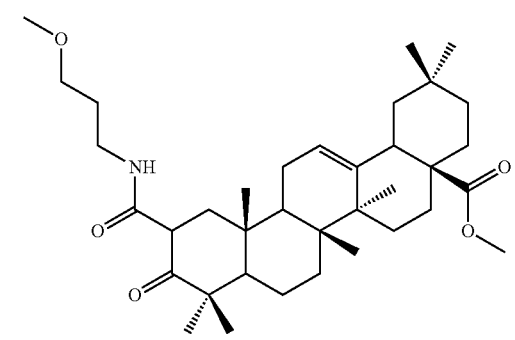
BS-OA-053
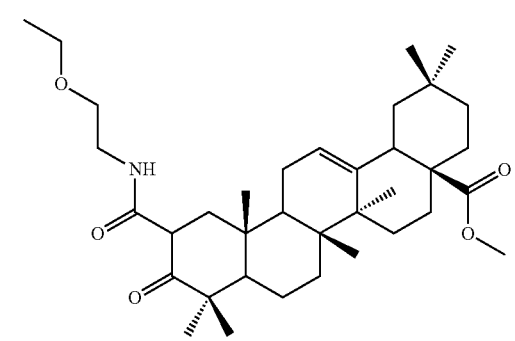
BS-OA-054
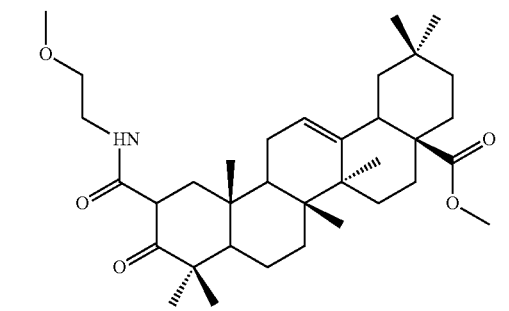

BS-OA-058
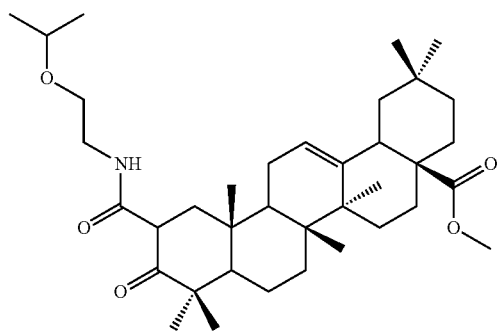
BS-OA-067
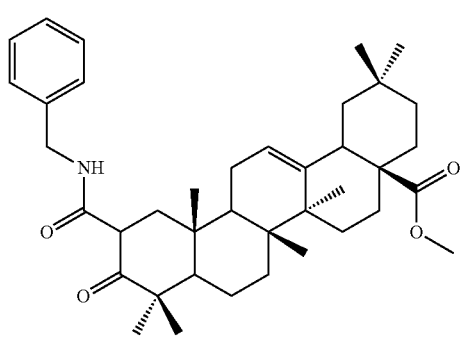
BS-OA-059
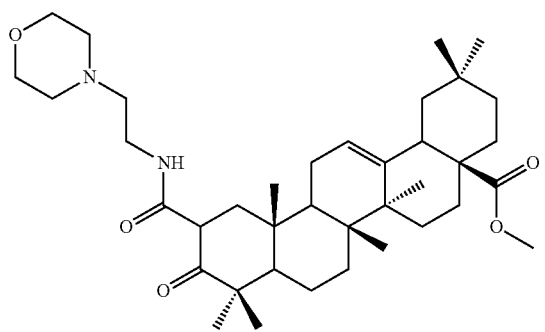
BS-OA-068
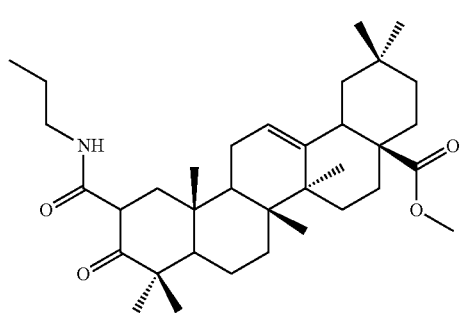
BS-OA-062
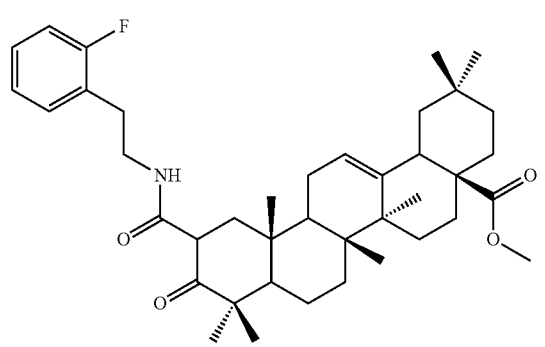
BS-OA-070
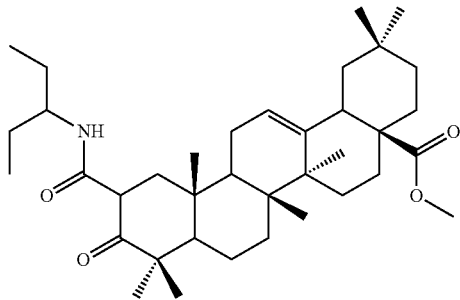
BS-OA-064
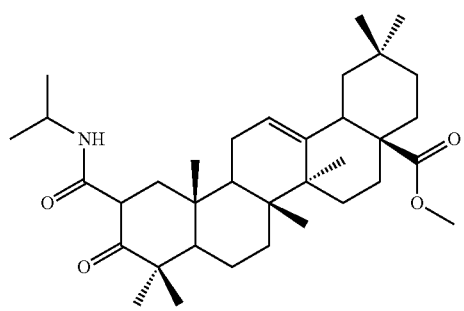
BS-OA-075
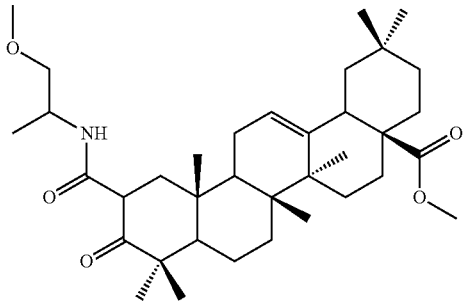

BS-OA-078
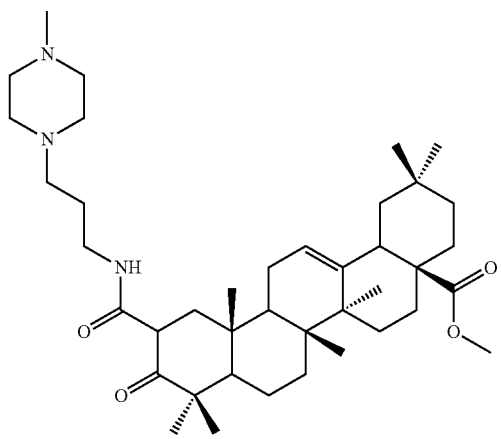
BS-OA-082
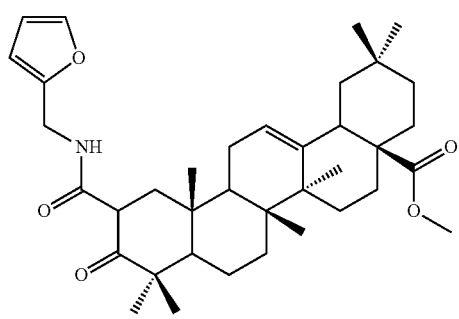
BS-OA-085
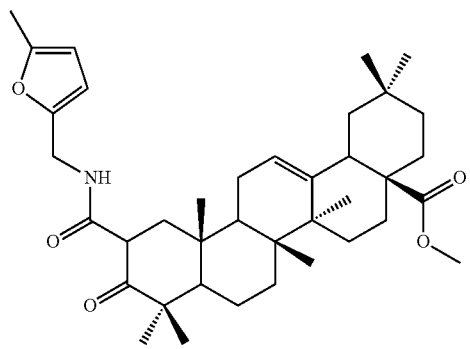
BS-OA-086
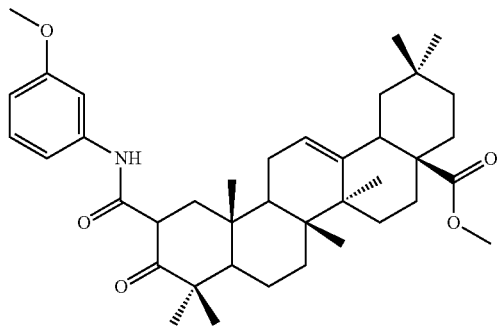
BS-OA-088
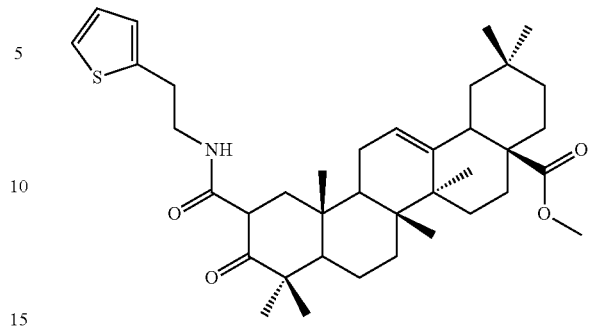
BS-OA-105
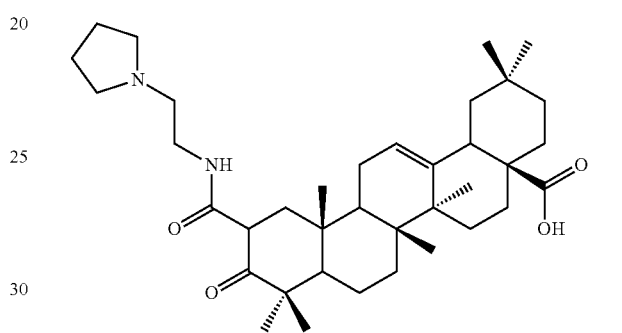
BS-OA-106
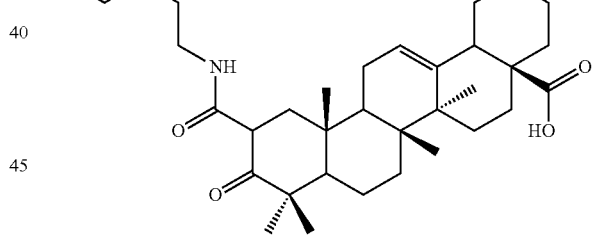
BS-OA-107
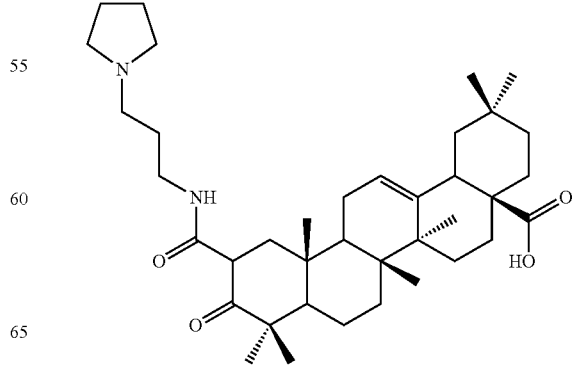

-continued

BS-OA-108

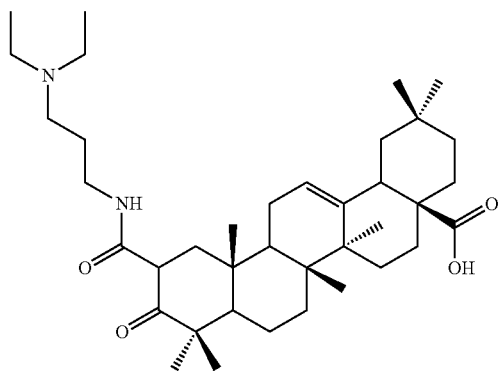

BS-OA-109

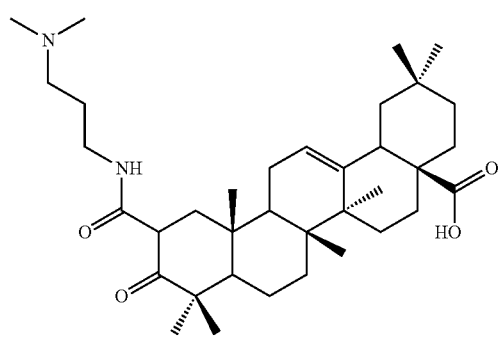

BS-OA-110

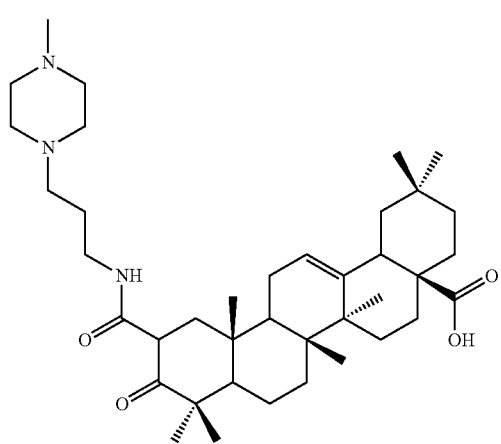

Some data for the above compounds are listed in the table below:

| Compound No. | Formula | Molecular Weight | Appearance | State | Total Yield (%) |
|---|---|---|---|---|---|
| BS-OA-003 | $C_{39}H_{53}F_2NO_4$ | 637.84 | White | Solid | 14.5 |
| BS-OA-004 | $C_{39}H_{62}N_2O_4$ | 622.92 | White | Solid | 14.1 |
| BS-OA-005 | $C_{38}H_{60}N_2O_4$ | 608.9 | White | Solid | 15.9 |
| BS-OA-008 | $C_{37}H_{59}NO_4$ | 581.87 | White | Solid | 14.6 |
| BS-OA-011 | $C_{36}H_{57}NO_4$ | 567.9 | White | Solid | 14.1 |
| BS-OA-012 | $C_{38}H_{62}N_2O_4$ | 610.9 | White | Solid | 16.9 |
| BS-OA-016 | $C_{39}H_{62}N_2O_4$ | 622.9 | White | Solid | 14.1 |
| BS-OA-017 | $C_{39}H_{54}FNO_4$ | 619.9 | White | Solid | 15.2 |
| BS-OA-021 | $C_{39}H_{54}FNO_4$ | 619.85 | White | Solid | 14.8 |
| BS-OA-024 | $C_{39}H_{53}F_2NO_4$ | 637.84 | White | Solid | 14.8 |
| BS-OA-027 | $C_{39}H_{53}F_2NO_4$ | 616.9 | White | Oil | 13.4 |
| BS-OA-028 | $C_{36}H_{55}NO_4$ | 565.8 | White | Solid | 15.2 |

-continued

| Compound No. | Formula | Molecular Weight | Appearance | State | Total Yield (%) |
|---|---|---|---|---|---|
| BS-OA-031 | $C_{37}H_{59}NO_4$ | 581.87 | White | Solid | 14.3 |
| BS-OA-032 | $C_{39}H_{56}N_2O_4$ | 616.87 | Yellow | Solid | 15.3 |
| BS-OA-033 | $C_{40}H_{56}FNO_4$ | 633.9 | White | Solid | 12.7 |
| BS-OA-034 | $C_{35}H_{53}NO_4$ | 551.8 | White | Solid | 16.3 |
| BS-OA-035 | $C_{39}H_{64}N_2O_4$ | 625 | White | Solid | 16.9 |
| BS-OA-037 | $C_{39}H_{62}N_2O_5$ | 638.9 | White | Solid | 12.5 |
| BS-OA-038 | $C_{37}H_{59}NO_5$ | 597.87 | White | Solid | 15.1 |
| BS-OA-042 | $C_{37}H_{60}N_2O_4$ | 596.9 | White | Solid | 20.7 |
| BS-OA-044 | $C_{40}H_{56}FNO_4$ | 633.88 | White | Solid | 14.7 |
| BS-OA-046 | $C_{40}H_{57}NO_5$ | 631.9 | White | Solid | 13.2 |
| BS-OA-048 | $C_{36}H_{55}NO_4$ | 565.8 | White | Solid | 14.8 |
| BS-OA-052 | $C_{36}H_{57}NO_5$ | 583.84 | White | Solid | 14 |
| BS-OA-053 | $C_{36}H_{57}NO_5$ | 583.9 | White | Solid | 14.3 |
| BS-OA-054 | $C_{35}H_{55}NO_5$ | 569.81 | White | Solid | 15.6 |
| BS-OA-058 | $C_{37}H_{59}NO_5$ | 597.87 | White | Solid | 15.1 |
| BS-OA-059 | $C_{38}H_{60}N_2O_5$ | 624.89 | Yellow | Solid | 12.9 |
| BS-OA-062 | $C_{40}H_{56}FNO_4$ | 633.9 | White | Solid | 12.9 |
| BS-OA-064 | $C_{35}H_{55}NO_4$ | 553.8 | White | Solid | 14.4 |
| BS-OA-067 | $C_{39}H_{55}NO_4$ | 601.9 | White | Oil | 13.8 |
| BS-OA-068 | $C_{35}H_{55}NO_4$ | 553.8 | White | Solid | 15.6 |
| BS-OA-070 | $C_{37}H_{59}NO_4$ | 581.9 | White | Solid | 16 |
| BS-OA-075 | $C_{36}H_{57}NO_5$ | 583.84 | White | Solid | 14.9 |
| BS-OA-078 | $C_{40}H_{65}N_3O_4$ | 652 | White | Solid | 16.9 |
| BS-OA-082 | $C_{37}H_{53}NO_5$ | 591.82 | Yellow | Solid | 16.4 |
| BS-OA-085 | $C_{38}H_{55}NO_5$ | 605.9 | White | Solid | 13.5 |
| BS-OA-086 | $C_{39}H_{55}NO_5$ | 617.86 | White | Solid | 13.1 |
| BS-OA-088 | $C_{38}H_{55}NO_4S$ | 621.9 | White | Oil | 13.7 |
| BS-OA-105 | $C_{37}H_{58}N_2O_4$ | 594.87 | White | Solid | 3.63 |
| BS-OA-106 | $C_{37}H_{60}N_2O_4$ | 596.88 | White | Solid | 2.89 |
| BS-OA-107 | $C_{38}H_{60}N_2O_4$ | 608.89 | White | Solid | 2.23 |
| BS-OA-108 | $C_{38}H_{62}N_2O_4$ | 610.91 | White | Solid | 2.93 |
| BS-OA-109 | $C_{36}H_{58}N_2O_4$ | 582.86 | White | Solid | 2.24 |
| BS-OA-110 | $C_{39}H_{63}N_3O_4$ | 637.94 | White | Solid | 2.14 |

According to another embodiment of the present invention, the following compounds of formula (I) are particularly preferred:

BS-OA-005

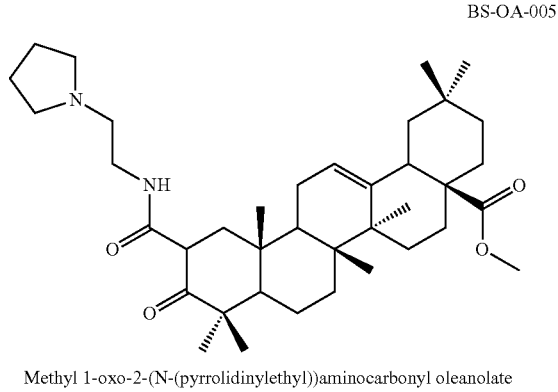

Methyl 1-oxo-2-(N-(pyrrolidinylethyl))aminocarbonyl oleanolate

-continued

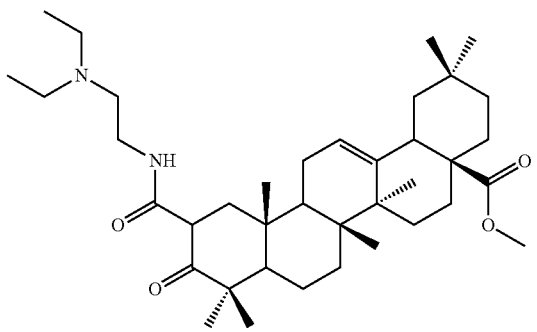

Methyl 1-oxo-2-(N-(diethylaminoethyl))aminocarbonyl oleanolate

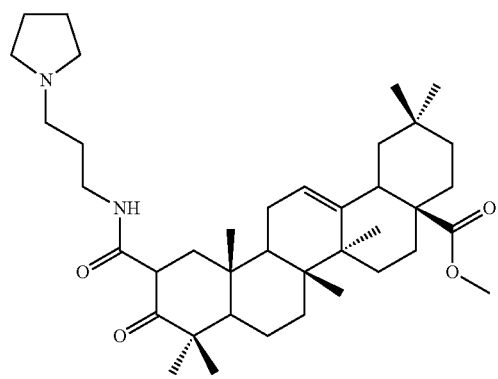

Methyl 1-oxo-2-(N-(pyrrolidinylpropyl))aminocarbonyl oleanolate

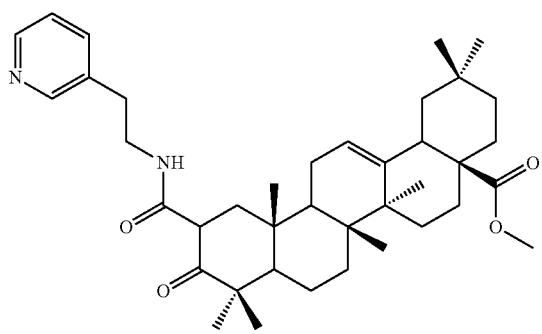

Methyl 1-oxo-2-(N-(3-pyridylethyl))aminocarbonyl oleanolate

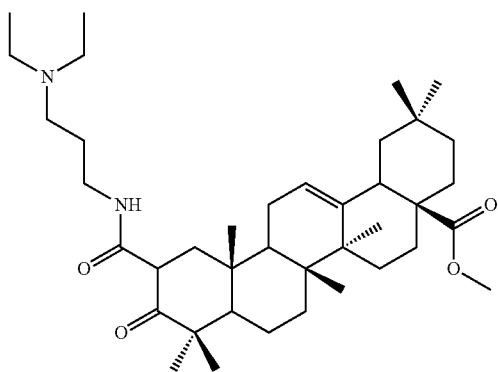

Methyl 1-oxo-2-(N-(diethylaminopropyl))aminocarbonyl oleanolate

-continued

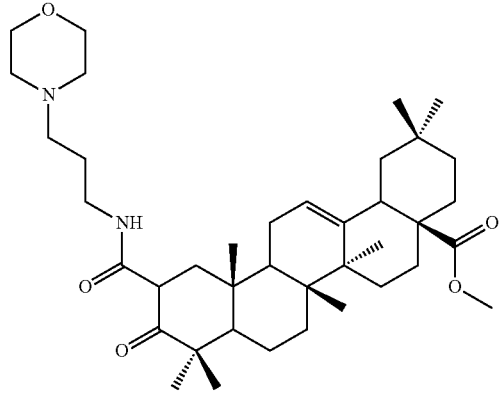

Methyl 1-oxo-2-(N-(morpholinypropyl))aminocarbonyl oleanolate

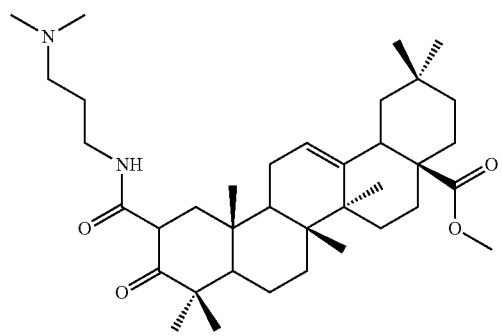

Methyl 1-oxo-2-(N-(dimethylaminopropyl))aminocarbonyl oleanolate

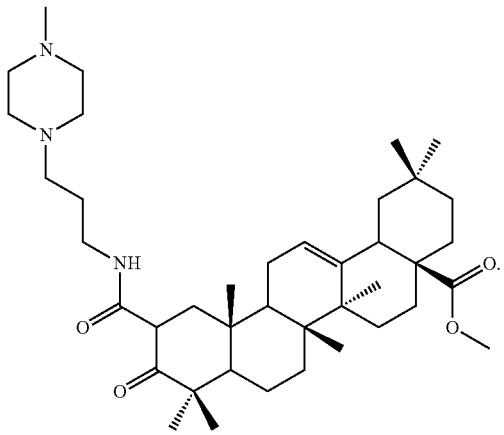

Methyl 1-oxo-2-(N-(N-methylpiperazinylpropyl))aminocarbonyl oleanolate

The 2-substituted oleanolic acid derivatives of the present invention have an antitumor activity. As compared with oleanolic acid per se, the 2-substituted oleanolic acid derivatives of the present invention have antitumor activities which are improved by such as several folds or even tens of folds.

As used herein, the term "alkyl" refers to a straight or branched radical containing designated number of carbon atoms derived from alkanes. The alkyl can comprise 1-18 carbon atoms, such as 1-12, 1-10, 1-8, 1-6, 1-5, 1-4 or 1-3 carbon atoms. Examples of the alkyl include, but not limited to, methyl, ethyl, n-propyl, isopropyl, tert-butyl, n-pentyl, n-hexyl and n-octadecyl.

The term "alkenyl" refers to a straight or branched alkenyl group containing designated number of carbon atoms. The alkenyl can comprise 2-18 carbon atoms, such as 2-12, 2-10, 2-8, 2-6, 2-5, 2-4 or 2-3 carbon atoms. Examples of alkenyl include, but not limited to, vinyl, allyl and octadecenyl.

The term "alkynyl" refers to a straight or branched alkynyl group containing designated number of carbon atoms. The alkynyl can comprise 2-18 carbon atoms, such as 2-12, 2-10, 2-8, 2-6, 2-5, 2-4 or 2-3 carbon atoms. Examples of alkynyl include, but not limited to, acetylenyl and propynyl.

The term "$C_3$-$C_7$ cycloalkyl or cycloalkenyl" refers to a saturated or unsaturated 3-7 membered monocyclic hydrocarbon radical. Representative examples of $C_3$-$C_7$ cycloalkyl or cycloalkenyl can be cyclopropyl, cyclobutyl, cyclopentyl, cyclohexyl, cycloheptyl, cyclopropenyl and cyclohexenyl.

The term "aryl" refers to a monocyclic aryl or polycyclic aryl, fused or unfused, containing 6-14 (such as 6-12, or 6-10) carbon atoms. In the case of polycyclic aryl, at least one ring is aromatic. Aryl can also be one fused with a heterocyclyl. Examples of aryl include phenyl, biphenyl, naphthyl, 5,6,7,8-tetrahydronaphthyl, 2,3-dihydrobenzofuranyl, etc.

The term "heteroaryl" refers to an aromatic ring group having 1-4 heteroatoms (e.g. 1, 2, 3 or 4 heteroatoms) in the ring as ring member(s). A heteroatom refers to nitrogen, oxygen or sulfur. A heteroaryl can be a monocyclic heteroaryl having 5-7 ring atoms or a bicyclic heteroaryl having 7-11 ring atoms. Said bicyclic heteroaryl should comprise at least one aromatic heterocyclic group, and the other ring(s) can be aromatic or non-aromatic, with or without a heteroatom. Examples of heteroaryl include such as pyrrolyl, pyrazolyl, imidazolyl, oxazolyl, pyridinyl, pyrimidinyl, furanyl, thiophenyl, isoxazolyl, indolyl, etc.

The term "heterocyclyl" refers to a non-aromatic cyclic group containing 1-4 heteroatoms (e.g. 1, 2, 3 or 4 heteroatoms) as ring member(s). A heteroatom refers to nitrogen, oxygen or sulfur. A heterocyclyl can be a monocyclic heterocyclyl having 4-8 ring atoms (such as 4-7 membered ring, 5-7 membered ring or 5-6 membered ring) or a bicyclic heterocyclyl having 7-11 ring atoms. A heterocyclyl can be aromatic or non-aromatic. Examples of heterocyclyl include azacyclobutyl, pyrrolidinyl, pyrrolinyl, tetrahydrofuranyl, dihydrofuranyl, piperazinyl, piperidinyl, morpholinyl, thiomorpholinyl, tetrahydropyranyl, tetrahydrothiophenyl, etc.

The term "halogen" refers to fluorine, chlorine, bromine or iodine.

The term "alkylamino" refers to an amino group substituted with one or two alkyls as defined above.

The term "alkoxy" refers to alkyl-O— radical, wherein the alkyl is defined as above.

The term "alkylthio" refers to alkyl-S— radical, wherein the alkyl is defined as above.

As used herein, the term "pharmaceutically acceptable salts of the compounds of formula (I)" can be exemplified as organic acid salts formed by an organic acid which comprises a pharmaceutically acceptable anion. These organic acid salts include, but not limited to, tosylate, methanesulfonate, malate, acetate, citrate, malonate, tartrate, succinate, benzoate, ascorbate, α-ketoglutarate, lactate, and α-glycerophosphate. Suitable inorganic salts may also be formed, including but not limited to, hydrochloride, sulfate, nitrate, bicarbonate and carbonate, phosphate, hydrobromate, hydriodate and the like.

A pharmaceutically acceptable salt may be obtained using standard procedures well known in the art, for example by reacting a sufficient amount of alkaline compound with a suitable acid that provides a pharmaceutically acceptable anion.

The main structure of the 2-substituted oleanolic acid derivatives of the present invention has eight chiral centers in the stereochemical structure represented by the structural formula (I). The stereochemical definitions and conventions used herein generally follow MCGRAW-HILL DICTIONARY OF CHEMICAL TERMS (S. P. Parker, Ed., McGraw-Hill Book Company, New York, 1984); and ELIEL, E. AND WILEN, S., STEREOCHEMISTRY OF ORGANIC COMPOUNDS (John Wiley & Sons, Inc., New York, 1994). Many organic compounds are present in optically active forms, i.e., they have the ability to rotate plane-polarized light.

The terms "treatment," "treating," "treat," and the like used herein refer generally to obtaining a desired pharmacological and/or physiological effect. The effect may be prophylactic in terms of completely or partially preventing a disease or symptoms thereof, and/or may be therapeutic in terms of partial or complete stabilization or cure of a disease and/or adverse effects caused by the disease. "Treatment" as used herein covers any treatment of a disease in a subject, including: (a) preventing the disease or symptoms from occurring in a subject who is predisposed to the disease or symptoms but has not yet been diagnosed as having it; (b) inhibiting the symptoms of a disease, i.e., arresting its development; or (c) relieving the symptoms of a disease, i.e., causing regression of the disease or symptoms.

The compounds of the present invention can be prepared through a conventional organic chemistry synthesis process. For example, the compound of formula (I) of the present invention is prepared as follows.

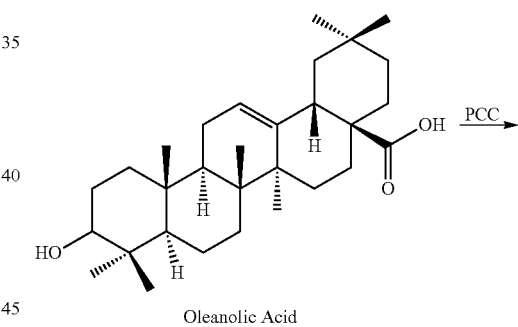

Oleanolic Acid

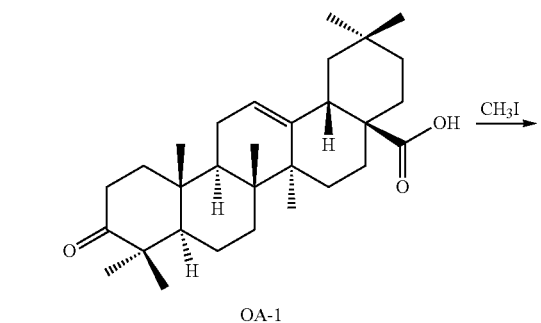

OA-1

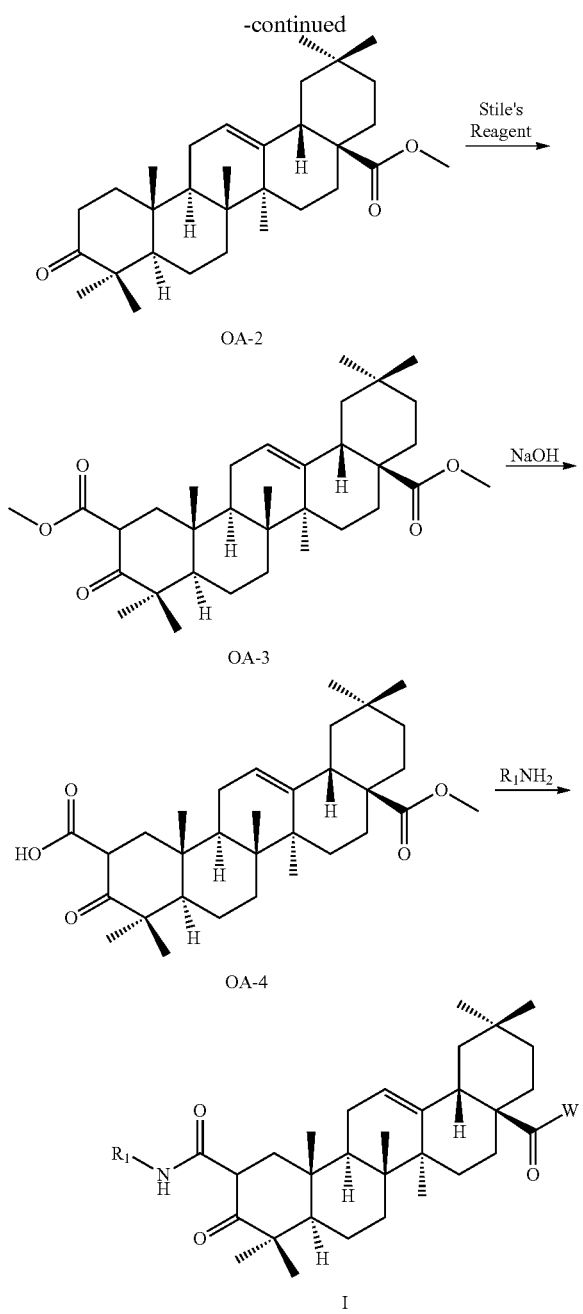

The 2-substituted oleanolic acid derivative of formula (I) can be prepared by subjecting oleanolic acid (OA) extracted from natural medicines to oxidation to produce a ketone intermediate of oleanolic acid (OA-1). Various types of oxidants can be used to oxidize a hydroxyl to a carbonyl, such as pyridinium chlorochromate (PCC), potassium permanganate, and the like.

The ketone intermediate of oleanolic acid (OA-1) is subjected to esterification to produce a methyl ester (ketone) intermediate of oleanolic acid (OA-2). Various types of methylation reactions can be used for the formation of methyl ester. For example, in the presence of an alkali in a polar solvent, methyl iodide can be used to form the methyl ester (ketone) intermediate of oleanolic acid (OA-2).

The methyl ester (ketone) intermediate of oleanolic acid (OA-2) reacts with Stile's Reagent, thereby introducing a methoxycarbonyl group to the ortho-position of the ketone carbonyl to produce a diester intermediate of oleanolic acid (OA-3). Various types of reagents can be used to introduce a methoxycarbonyl group to the ortho-position of the ketone carbonyl. For example, methoxymagnesium methyl carbonate can be used in a polar solvent to introduce a methoxycarbonyl group to the ortho-position of the ketone carbonyl with good yield and produce a diester intermediate of oleanolic acid (OA-3).

The diester intermediate of oleanolic acid (OA-3) is hydrolyzed with NaOH in a polar solvent to produce a monocarboxyl intermediate of oleanolic acid (OA-4). Other organic alkali or inorganic alkali can also be used to obtain the monocarboxyl intermediate of oleanolic acid (OA-4).

After the introduction of the methoxycarbonyl group, the diester intermediate of oleanolic acid (OA-3) may be directly hydrolyzed without separation to obtain the monocarboxyl intermediate of oleanolic acid (OA-4).

The monocarboxyl intermediate of oleanolic acid (OA-4) is subjected the to an amido bond formation reaction with an organic amine to produce the 2-substituted oleanolic acid derivative (I).

The organic amines for the amidation are all commercially available.

The amidation reaction typically occurs in the presence of a condensing agent, wherein the condensing agent can be, but not limited to, an organic condensing agent, such as 2-(7-azobenzotriazolyl)-N,N,N',N'-tetramethyluronium hexafluorophosphate (HATU), benzotriazolyl-N,N,N',N'-tetramethyluronium hexafluoroborate (HBTU), (benzotriazol-1-yloxy)tris(dimethylamino)phosphonium hexafluorophosphate (BOP), benzotriazolyl-N,N,N',N'-tetramethyluronium hexafluoroborate (TBTU), and tripropylphosphoric anhydride ($T_3P$).

The amidation reaction is typically carried out in the presence of an alkali. The alkali herein can be, but not limited to, an organic alkali, such as N,N-diisopropylethylamine (DIPEA), triethylamine (TEA), pyridine or 4-dimethylaminopyridine (DMAP).

The amidation reaction is typically carried out in a solvent and it may also be carried out in the absence of a solvent. The solvent used herein includes, but not limited to, organic polar solvents, such as dichloromethane (DCM), tetrahydrofuran (THF), N,N-dimethylformamide (DMF) or dimethylsulfoxide (DMSO), etc.

Conventional chemical conversion processes may be used to practice this invention. One skilled person in the art can determine suitable chemical agents, solvents, protecting groups, and reaction conditions for these chemical conversions. Relevant information are described, for example, in R. Larock, *Comprehensive Organic Transformations*, VCH Publishers (1989); T. W. Greene and P. G. M. Wuts, *Protective Groups in Organic Synthesis*, $3^{rd}$ Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

Protecting groups refer to the groups that, upon being attached to an active moiety (e.g., a hydroxyl or amino group), prevent the moiety from being interfered in a subsequent reaction and, after the reaction, can be removed through a conventional method. Examples of a hydroxyl protecting group include, but not limited to, alkyl, benzyl, allyl, trityl (also known as triphenylmethyl), acyl (e.g., benzoyl, acetyl, or HOOC—X"—CO—, wherein X" is alkylidene, alkenylene, cycloalkylene, or arylene), silyl (e.g., trimethylsilyl, triethylsilyl, and t-butyldimethylsilyl), alkoxylcarbonyl, aminocarbonyl (e.g., dimethylaminocarbonyl, methylethylaminocarbonyl, and phenylaminocarbonyl), alkoxymethyl, benzyloxymethyl, and alkylmercaptomethyl. Examples of an amino protecting group include, but not limited to, alkoxycarbonyl, alkanoyl, aryloxycarbonyl, aryl-substituted alkyl and the like. Hydroxyl and amino protecting groups have been discussed in T. W. Greene and P. G. M. Wuts, Protective Groups in Organic Synthesis, 2nd. Ed., John Wiley and Sons (1991). All hydroxyl and amino protecting groups can be removed by a conventional method after the reaction.

Specifically, among the preferred compounds of formula (I) of the present invention, BS-OA-067, BS-OA-003, BS-OA-004, BS-OA-005, BS-OA-008, BS-OA-011, BS-OA-012, BS-OA-016, BS-OA-017, BS-OA-021, BS-OA-024, BS-OA-027, BS-OA-028, BS-OA-031, BS-OA-032, BS-OA-033, BS-OA-034, BS-OA-035, BS-OA-037, BS-OA-038, BS-OA-042, BS-OA-044, BS-OA-046, BS-OA-048, BS-OA-052, BS-OA-053, BS-OA-054, BS-OA-058, BS-OA-059, BS-OA-062, BS-OA-064, BS-OA-068, BS-OA-070, BS-OA-075, BS-OA-078, BS-OA-082, BS-OA-085, BS-OA-086 and BS-OA-088 are prepared directly according to the above reaction procedure.

On the other hand, BS-OA-105, BS-OA-106, BS-OA-107, BS-OA-108, BS-OA-109 and BS-OA-110 are prepared by firstly protecting the 28-hydroxyl with a Bn protecting group and then removing the protecting group through a conventional process after the reaction.

The present invention also provides a pharmaceutical composition comprising the compound of formula (I) of the present invention.

The present invention provides a pharmaceutical composition which comprises at least one compound of formula (I) of the present invention as defined above and optionally a pharmaceutically acceptable excipient.

The methods for preparing various pharmaceutical compositions having a given amount of active components are known or will be apparent to those skilled in the art in light of this disclosure. As described in REMINGTON'S PHARMACEUTICAL SCIENCES, Martin, E. W., ed., Mack Publishing Company, 19th ed. (1995), the methods for preparing such pharmaceutical compositions include incorporation of other suitable pharmaceutical excipients, carriers, diluents, etc.

The pharmaceutical preparations of the present invention are produced by known methods, including mixing, dissolving, or freeze drying processes.

The compounds of the present invention may be formulated into a pharmaceutical composition and administered to a subject in a route suitable for the selected administration manner, e.g., orally, by gastrointestinal perfusion, or by intravenous, intramuscular or subcutaneous injection.

Thus, the present compounds may be systemically administered, e.g., orally administered, in combination with a pharmaceutically acceptable carrier such as an inert diluent or an edible carrier. They may be enclosed in hard or soft gelatin capsules, or may be compressed into tablets. For therapeutic oral administration, the active compound may be combined with one or more excipients and may be taken in a form of ingestible tablet, buccal tablet, troche, capsule, elixir, suspension, syrup, wafer, and the like. Such a composition or preparation should contain at least 0.1% of the active compound. Of course, the proportion of active compound in the compositions and preparations may vary and may be from about 1% to about 99% by weight of a given unit dosage form. In a therapeutically useful composition, the active compound is present in an amount such that an effective dosage level is achieved.

A tablet, troche, pill, capsule and the like may also comprise a binder, such as gum tragacanth, arabic gum, corn starch or gelatin; an excipient such as calcium dihydrogenphosphate; a disintegrating agent such as corn starch, potato starch, alginic acid and the like; a lubricant such as magnesium stearate; and a sweetening agent such as sucrose, fructose, lactose or aspartame; or a flavoring agent such as peppermint, wintergreen oil, or cherry flavor. In case the unit dosage form is a capsule, it may comprise, in addition to the above materials, a liquid vehicle such as a vegetable oil or polyethylene glycol. Various other materials may be present as coatings or otherwise modify the physical form of the solid unit dosage form. For instance, a tablet, pill, or capsule may be coated with gelatin, wax, shellac or sugar, etc. A syrup or elixir may contain an active compound, a sweetening agent such as sucrose or fructose, a preservative such as methylparaben or propylparaben, a dye and a flavoring agent (such as cherry or orange flavor). Of course, any materials used in preparing unit dosage forms should be pharmaceutically acceptable and substantially non-toxic in the amounts employed. In addition, the active compound may be incorporated into a sustained-release preparation or device.

The active compound may also be administered intravenously or intraperitoneally by infusion or injection. An aqueous solution of the active compound or its salt may be prepared, optionally mixed with a nontoxic surfactant. Also can be prepared is dispersion in glycerol, liquid polyethylene glycol, triacetin, or a mixture thereof, or in an oil. Under ordinary storage and use conditions, these preparations contain a preservative to prevent the growth of microorganisms.

The pharmaceutical dosage forms suitable for injection or infusion may include a sterile aqueous solution, a dispersion or a sterile powder comprising active ingredients (optionally encapsulated in liposomes), which are adapted for an extemporaneous preparation of sterile injectable or infusible solution or dispersion. In all cases, the final dosage form must be sterile and stable liquids under the manufacture and storage conditions. The liquid carrier or vehicle may be a solvent or a liquid dispersion medium comprising, for example, water, ethanol, a polyol (for example, glycerol, propylene glycol, liquid polyethylene glycol, and the like), a vegetable oil, a nontoxic glyceride, and a suitable mixture thereof. A proper fluidity can be maintained, for example, by formation of liposomes, by maintenance of the required particle size in the case of dispersion or by the use of a surfactant. The prevention of microorganism can be achieved by various antibacterial and antifungal agents, such as parabens, chlorobutanol, phenol, sorbic acid, thimerosal, and the like. In many cases, an isotonic agent is preferably comprised, such as sugar, buffer agent or sodium chloride. Prolonged absorption of an injectable composition can be obtained by the use of a composition of the agents for delaying absorption, for example, aluminum monostearate and gelatin.

An injectable sterile solution is prepared by combining a required amount of the active compound in a suitable solvent with various additional desired components as listed above, followed by filtration and sterilization. For sterile powder used to prepare an injectable sterile solution, the preferred preparation process is vacuum drying and freeze drying techniques, which yield a powder of the active ingredient plus any additional desired ingredient present in the previous filtered sterile solution.

Useful solid carriers include finely divided solids such as talc, clay, microcrystalline cellulose, silica, alumina and the like. Useful liquid carriers include water, ethanol or ethylene glycol or a water-ethanol/ethylene glycol mixture, in which the compound of the present invention can be dissolved or dispersed at an effective content, optionally with the aid of a non-toxic surfactant. An adjuvant (such as a flavour) and additional antimicrobial agent can be added to optimize the properties for a given application.

Thickening agent (such as a synthetic polymer, a fatty acid, a fatty acid salt and ester, a fatty alcohol, a modified cellulose or a modified inorganic material) can also be used with a liquid carrier to form a spreadable paste, gel, ointment, soap and the like for applying directly to the skin of a user.

The amount of the compound or an active salt or derivative thereof required for a treatment varies depending not only on the selected particular salt but also on the administration route, the nature of the condition to be treated and the age and condition of the subject, and will be ultimately determined at the discretion of the attendant physician or clinician.

The above formulations can be present in a unit dosage form which is a physically discrete unit containing a unit dosage, which is suitable for administering to a human or other mammalians. The unit dosage form may be a capsule or a tablet, or a plurality of capsules or tablets. Depending upon the intended particular therapy, the amount of the active ingredient in a unit dosage form can be varied or adjusted in the range of about 0.1 mg to about 1,000 mg or more.

The present invention also provides the use of a compound according to the present invention or a pharmaceutical composition comprising the compound of the present invention in manufacture of a medicament, especially an antitumor medicament. Accordingly, the present invention provides a method for treating a subject suffering from tumor, comprising administering to the subject in need thereof a therapeutically effective amount of at least one compound of the present invention. The 2-substituted oleanolic acid derivative of the present invention or a pharmaceutically acceptable salt thereof can be used, for example, for the treatment of leukemia, multiple myeloma, lymphoma, liver cancer, gastric cancer, breast cancer, cholangiocellular carcinoma, pancreatic cancer, lung cancer, colorectal cancer, osteosarcoma, melanoma, cervical cancer, glioma, nasopharyngeal carcinoma, laryngeal carcinoma, esophageal cancer, middle ear tumor, prostate cancer, etc.

The present invention will be explained in more detailed by the following examples. However, it should be understood that the following examples are intended for illustration only but not to limit the scope of the present invention in any way.

The raw chemicals used in the following examples are commercially available or may be prepared by a synthesis method known in the art.

EXAMPLE 1

Synthesis of Compound BS-OA-067

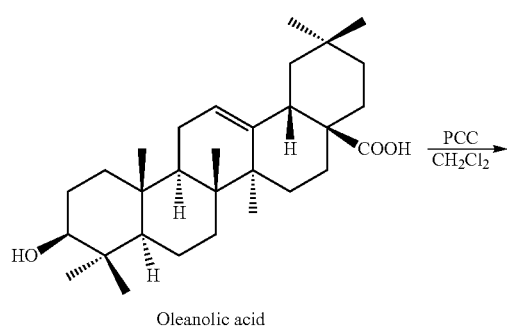

Oleanolic acid

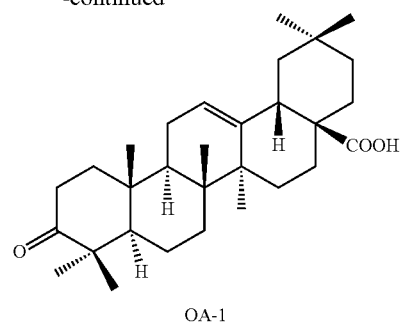

OA-1 wherein, PCC is pyridinium chlorochromate.

Oleanolic acid (147 g, 0.32 mmol) and pyridinium chlorochromate (81.9 g, 0.38 mol) are added to dichloromethane (1500 mL). The reaction solution is stirred overnight under room temperature. When the reaction is completed, the reaction solution is filtered. The crude product resulted from concentrating the filtrate is separated and purified via a silica-gel column to give compound OA-1 (123 g, 84.66%) as a white solid.

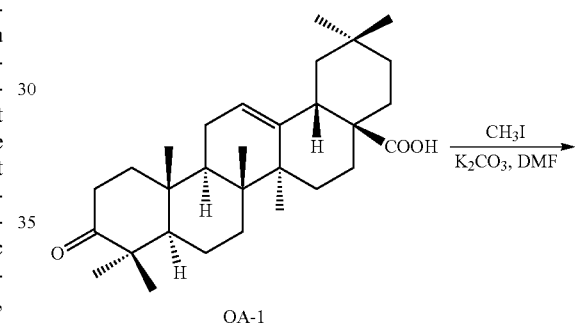

OA-1

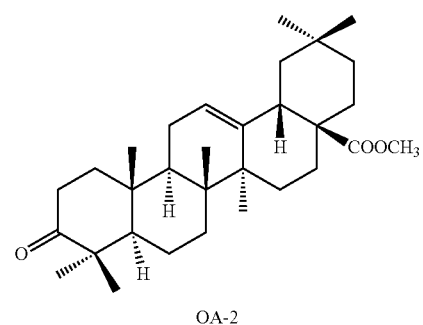

OA-2

To N,N-dimethylformamide (800 mL) are added the compound OA-1 (63 g, 0.14 mol) and potassium carbonate (23.18 g, 0.168 mol), followed by the addition of methyl iodide (23.86 g, 0.168 mol) all at once. The reaction solution is stirred for 5 hours under room temperature. When the reaction is completed, the reaction solution is concentrated. Water is added to the crude product resulted from concentration and dichloromethane is used for extraction. The organic phase is dried with anhydrous sodium sulfate. The crude product resulted from concentrating the organic phase is separated and purified via a silica-gel column to give compound OA-2 (41.5 g, 63.34%) as a white solid.

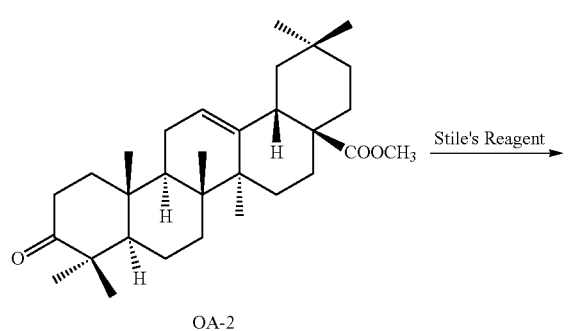

OA-2

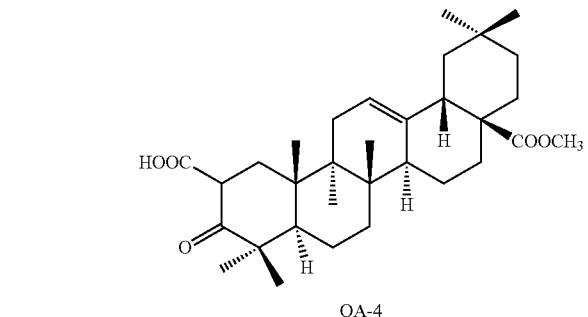

OA-4 wherein the Stile's Reagent is methoxymagnesium methyl carbonate of 2M dissolved in N,N-dimethylformamide Under nitrogen protection, a mixed solution of the compound OA-2 (7.15 g, 15.28 mmol) and Stile's Reagent (73 mL) is heated up to 110° C. After the reaction solution is stirred for 1.5 hours, hydrochloric acid (5%) is injected into the reaction solution, which is then extracted with ethyl acetate (100 mL*3). The organic phase is washed with water (100 mL*3), dried with anhydrous sodium sulfate, and concentrated to give compound OA-4 (4.68 g, 59.85%) as a white solid.

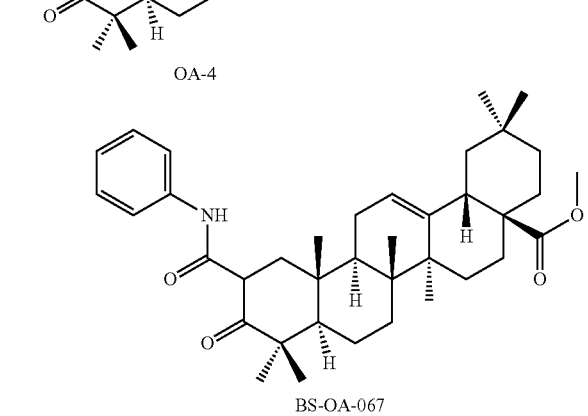

OA-4

BS-OA-067 wherein T3P is tripropylphosphoric anhydride.

To 2 mL dichloromethane are added the compound OA-4 (130 mg, 0.253 mmol), and benzylamine (27 mg, 0.253 mmol), followed by the addition of tripropylphosphoric anhydride (80.4 mg, 0.253 mmol) The reaction solution is agitated for 16 hours under 30° C. When the reaction is completed, the reaction solution is directly separated and purified via preparative thin layer chromatography to give compound BS-OA-067 (21.1 mg, 13.8%) as a white oil.

LC-MS: retention time: 2.402 min (8.890%, isomer), 2.826 min (89.645%), m/z: 602.4 (M+H).

$^1$H NMR (CDCl$_3$, 400 MHz): δ 7.375-7.253 (m, 5H), 5.615-5.603 (d, J=4.8 Hz, 1H), 5.292 (s, 1H), 4.576-4.525 (m, 1H), 4.450-4.403 (m, 1H), 3.624 (s, 3H), 2.875-2.851 (d, J=9.6 Hz, 1H), 2.003-1.950 (m, 3H), 1.874-1.733 (m, 2H), 1.628-1.597 (m, 5H), 1.536-1.450 (m, 4H), 1.351-1.326 (m, 2H), 1.197-1.104 (m, 13H), 1.088-0.951 (m, 9H), 0.915 (s, 3H).

BS-OA-003 is prepared according to the process for BS-OA-067 using the same reagents as above by reacting the compound OA-4 with 3,4-difluorobenzylamine.

LC-MS: retention time: 2.52 min (8.16%, isomer), 2.93 min (82.50%), m/z: 638.3 (M+H).

$^1$H NMR (400 MHz, CDCl$_3$): δ 7.147 (m, 2H), 7.001 (s, 1H), 5.292 (t, 1H), 3.620 (s, 3H), 2.842 (m, 1H), 2.055-1.826 (m, 4H), 1.785 (d, 1H), 1.684-1.594 (m, 4H), 1.536-1.415 (m, 4H), 1.382-1.245 (m, 3H), 1.175-1.097 (m, 13H), 0.950-0.884 (m, 9H), 0.769 (s, 3H).

BS-OA-004 is prepared according to the process for BS-OA-067 using the same reagents as above by reacting the compound OA-4 with 1-piperidineethylamine.

LC-MS: retention time: 1.81 min (92.73%), m/z: 623.4 (M+H).

$^1$H NMR (400 MHz, CDCl$_3$): δ 5.360 (t, 1H), 3.648 (s, 3H), 3.408 (s, 2H), 2.927 (m, 1H), 2.583 (m, 5H), 2.044-1.958 (m, 4H), 1.790-1.634 (m, 11H), 1.555-1.442 (m, 6H), 1.394-1.297 (m, 3H), 1.233-1.070 (m, 12H), 0.956-0.924 (m, 9H), 0.792 (s, 3H).

BS-OA-005 is prepared according to the process for BS-OA-067 using the same reagents as above by reacting the compound OA-4 with 1-pyrrolidinylethylamine.

LC-MS: retention time: 1.77 min (93.89%), m/z: 609.4 (M+H).

$^1$H NMR (400 MHz, CDCl$_3$): δ 6.106 (s, 1H), 5.350 (t, 1H), 3.629 (s, 3H), 3.517-3.290 (m, 2H), 2.912-2.869 (m, 1H), 2.681-2.574 (m, 6H), 2.074-1.912 (m, 4H), 1.891-1.611 (m, 10H), 1.547-1.453 (m, 3H), 1.428-1.289 (m, 3H), 1.232-1.050 (m, 13H), 0.989-0.898 (m, 9H), 0.776 (s, 3H).

BS-OA-008 is prepared according to the process for BS-OA-067 using the same reagents as above by reacting the compound OA-4 with 2-methylbutylamine LC-MS: retention time: 2.71 min (50.06%, isomer), 2.98 min (44.45%), m/z: 582.3 (M+H), 604.3 (M+Na).

$^1$H NMR (400 MHz, CDCl$_3$): δ 5.333 (m, 1H), 3.620 (s, 3H), 3.157 (m, 1H), 2.875 (m, 1H), 2.577 (m, 1H), 2.370 (m, 1H), 1.998-1.839 (m, 5H), 1.763-1.603 (m, 7H), 1.476-1.385 (m, 3H), 1.370-1.296 (m, 4H), 1.193-1.032 (m, 15H), 0.945-0.890 (m, 9H), 0.769 (s, 3H).

BS-OA-011 is prepared according to the process for BS-OA-067 using the same reagents as above by reacting the compound OA-4 with isobutylamine LC-MS: retention time: 2.72 min (17.02%, isomer), 2.89 min (79.56%), m/z: 568.3 (M+H), 590.4 (M+Na).

$^1$H NMR: (400 MHz, CDCl$_3$): δ 5.329 (t, 1H), 3.626 (s, 3H), 3.314 (m, 1H), 2.874 (m, 1H), 2.525-2.314 (m, 1H), 2.000-1.842 (m, 4H), 1.743-1.535 (m, 6H), 1.528-1.387 (m, 3H), 1.408-1.244 (m, 3H), 1.198-1.029 (m, 15H), 0.934-0.891 (m, 9H), 0.766 (s, 3H).

BS-OA-012 is prepared according to the process for BS-OA-067 using the same reagents as above by reacting the compound OA-4 with N,N-diethylethylenediamine.

LC-MS: retention time: 1.82 min (94.04%), m/z: 611.4 (M+H).

1H NMR: (400 MHz, CDCl$_3$): δ 6.265 (s, 1H), 5.382-5.297 (m, 1H), 3.629 (s, 3H), 3.326 (m, 2H), 2.913-2.869 (m, 1H), 2.560 (m, 6H), 2.062-1.866 (m, 4H), 1.745-1.617 (m, 6H), 1.548-1.424 (m, 4H), 1.390-1.303 (m, 3H), 1.215-1.106 (m, 9H), 1.099-1.021 (m, 9H), 0.989-0.886 (m, 9H), 0.786 (s, 3H).

BS-OA-016 is prepared according to the process for BS-OA-067 using the same reagents as above by reacting the compound OA-4 with 1-pyrrolidinepropylamine.

LC-MS: retention time: 1.79 min (93.26%), m/z: 623.4 (M+H).

$^1$H NMR: (400 MHz, CDCl$_3$): δ 7.143 (s, 1H), 5.320-5.303 (m, 1H), 3.623 (s, 3H), 3.567-3.513 (m, 1H), 3.492-3.302 (m, 1H), 2.892-2.653 (m, 7H), 2.140-1.925 (m, 4H), 1.820-1.558 (m, 12H), 1.543-1.422 (m, 3H), 1.415-1.265 (m, 3H), 1.223-1.034 (m, 13H), 0.977-0.856 (m, 9H), 0.783 (s, 3H).

BS-OA-017 is prepared according to the process for BS-OA-067 using the same reagents as above by reacting the compound OA-4 with p-fluorobenzylamine.

LC-MS: retention time: 2.40 min (7.08%, isomer), 2.81 min (86.17%), m/z: 620.3 (M+H), 642.3 (M+Na).

$^1$H NMR: (400 MHz, CDCl$_3$): δ 7.305 (t, 2H), 7.072 (t, 2H), 5.323 (m, 1H), 3.644 (s, 3H), 3.314 (m, 1H), 2.864 (m, 1H), 2.064-1.894 (m, 3H), 1.651-1.637 (m, 5H), 1.545-1.455 (m, 3H), 1.404-1.316 (m, 3H), 1.232-1.072 (m, 15H), 0.970-0.906 (m, 9H), 0.792 (s, 3H).

BS-OA-021 is prepared according to the process for BS-OA-067 using the same reagents as above by reacting the compound OA-4 with 3-fluorobenzylamine.

LC-MS: retention time: 2.40 min (7.28%, isomer), 2.82 min (90.96%), m/z: 620.3 (M+H), 642.3 (M+Na).

$^1$H NMR: (400 MHz, CDCl$_3$): δ 7.099 (d, 1H), 7.032 (m, 2H), 5.329 (m, 1H), 3.646 (s, 3H), 2.913 (m, 1H), 2.066-1.932 (m, 3H), 1.87 (d, 1H), 1.204-1.125 (m, 12H), 0.979-0.907 (m, 9H), 0.793 (s, 3H).

BS-OA-024 is prepared according to the process for BS-OA-067 using the same reagents as above by reacting the compound OA-4 with 2,4-difluorobenzylamine.

LC-MS: retention time: 2.43 min (5.26%, isomer), 2.84 min (87.75%), m/z: 638.3 (M+H).

$^1$H NMR: (400 MHz, CDCl$_3$): δ 7.394 (m, 1H), 6.894 (m, 2H), 5.346 (m, 1H), 3.647 (s, 3H), 2.910 (m, 1H), 2.070-1.893 (m, 3H), 1.789 (d, 1H), 1.184-1.111 (m, 12H), 0.963-0.914 (m, 9H), 0.784 (s, 3H).

BS-OA-027 is prepared according to the process for BS-OA-067 using the same reagents as above by reacting the compound OA-4 with 2-(3-pyridinyl)ethylamine.

LC-MS: retention time: 1.66 min (93.28%), m/z: 617.4 (M+H), 639.2 (M+Na).

$^1$H NMR: (400 MHz, CDCl$_3$): δ 8.507-8.468 (m, 2H), 7.557 (d, J=8 Hz, 1H), 7.278 (d, J=8.4 Hz, 1H), 5.445 (m, 1H), 3.627 (s, 3H), 3.539 (m, 2H), 2.873 (m, 2H), 2.034-1.926 (m, 3H), 1.861-1.776 (m, 2H), 1.718-1.534 (m, 6H), 1.500-1.293 (m, 5H), 1.204-1.042 (m, 12H), 0.930-0.899 (m, 9H), 0.768 (s, 3H).

BS-OA-028 is prepared according to the process for BS-OA-067 using the same reagents as above by reacting the compound OA-4 with cyclobutylamine.

LC-MS: retention time: 2.72 min (17.15%, isomer), 2.88 min (78.71%), m/z: 566.3 (M+H), 588.3 (M+Na).

$^1$H NMR: (400 MHz, CDCl$_3$): δ 5.335 (m, 1H), 3.633 (s, 3H), 2.912 (m, 1H), 2.348 (m, 2H), 2.087-1.821 (m, 5H), 1.377-1.299 (m, 3H), 1.154-1.038 (m, 12H), 0.945-0.895 (m, 9H), 0.795 (s, 3H).

BS-OA-031 is prepared according to the process for BS-OA-067 using the same reagents as above by reacting the compound OA-4 with isopentylamine.

LC-MS: retention time: 2.71 min (48.11%, isomer), 2.98 min (48.67%), m/z: 582.4 (M+H), 604.3 (M+Na).

$^1$H NMR: (400 MHz, CDCl$_3$): δ 5.329 (m, 1H), 3.626 (s, 3H), 3.314 (m, 1H), 2.874 (m, 1H), 2.525-2.314 (m, 1H), 2.000-1.842 (m, 4H), 1.743-1.535 (m, 6H), 1.528-1.387 (m, 3H), 1.408-1.244 (m, 3H), 1.198-1.029 (m, 15H), 0.934-0.891 (m, 9H), 0.766 (s, 3H).

BS-OA-032 is prepared according to the process for BS-OA-067 using the same reagents as above by reacting the compound OA-4 with 2-(2-pyridinyl)ethylamine.

LC-MS: retention time: 1.80 min (91.55%), m/z: 617.4 (M+H), 639.3 (M+Na).

$^1$H NMR: (400 MHz, CDCl$_3$): δ 8.538 (m, 1H), 7.697 (m, 1H), 7.244 (m, 2H), 6.967 (m, 1H), 5.399 (m, 1H), 3.748-3.656 (m, 5H), 3.032 (m, 2H), 2.926 (m, 1H), 2.066-1.956 (m, 4H), 1.783-1.636 (m, 3H), 1.601-1.474 (m, 7H), 1.434-1.323 (m, 3H), 1.280-1.045 (m, 12H), 0.969-0.936 (m, 9H), 0.797 (s, 3H).

BS-OA-033 is prepared according to the process for BS-OA-067 using the same reagents as above by reacting the compound OA-4 with p-fluorophenylethylamine.

LC-MS: retention time: 2.85 min (91.30%), m/z: 634.3 (M+H).

$^1$H NMR: (400 MHz, CDCl$_3$): δ 7.164 (m, 2H), 7.026 (m, 2H), 3.632 (s, 3H), 2.910-2.799 (m, 3H), 2.035 (m, 2H), 1.502-1.446 (m, 2H), 1.376-1.308 (m, 3H), 1.163-1.089 (m, 12H), 0.939-0.904 (m, 9H), 0.772 (s, 3H).

BS-OA-034 is prepared according to the process for BS-OA-067 using the same reagents as above by reacting the compound OA-4 with cyclopropylamine.

LC-MS: retention time: 2.73 min (94.54%), m/z: 552.3 (M+H), 574.3 (M+Na).

$^1$H NMR: (400 MHz, CDCl$_3$): δ 5.445 (m, 1H), 3.626 (s, 3H), 2.891 (m, 1H), 2.699 (m, 1H), 2.061-1.855 (m, 4H), 1.715-1.680 (m, 2H), 1.642-1.541 (m, 5H), 1.504-1.443 (m, 3H), 1.405-1.291 (m, 3H), 1.247-1.047 (m, 12H), 0.929-0.894 (m, 9H), 0.811-0.721 (m, 5H), 0.524 (m, 2H).

BS-OA-035 is prepared according to the process for BS-OA-067 using the same reagents as above by reacting the compound OA-4 with N,N-diethylpropanediamine.

LC-MS: retention time: 1.79 min (93.86%), m/z: 625.4 (M+H).

$^1$H NMR: (400 MHz, CDCl$_3$): δ 7.480 (s, 1H), 5.333-5.314 (m, 1H), 3.650 (s, 3H), 3.453-3.404 (m, 2H), 2.921-2.887 (m, 1H), 2.635-2.561 (m, 6H), 2.085-1.916 (m, 4H), 1.744-1.633 (m, 8H), 1.565-1.473 (m, 4H), 1.402-1.367 (m, 3H), 1.182-1.151 (m, 9H), 1.103 (m, 9H), 0.958-0.930 (m, 9H), 0.794 (s, 3H).

BS-OA-037 is prepared according to the process for BS-OA-067 using the same reagents as above by reacting the compound OA-4 with 4-morpholinepropylamine.

LC-MS: retention time: 1.66 min (93.32%), m/z: 639.4 (M+H).

$^1$H NMR: (400 MHz, CDCl$_3$): δ 5.320 (m, 1H), 3.724 (s, 4H), 3.619 (d, 3H), 3.312 (m, 2H), 2.887 (m, 1H), 2.450 (m, 6H), 2.080-1.897 (m, 4H), 1.765-1.603 (m, 8H), 1.535-1.409 (m, 4H), 1.355-1.291 (m, 3H), 1.199-1.060 (m, 12H), 0.940-0.893 (m, 9H), 0.776 (s, 3H).

BS-OA-038 is prepared according to the process for BS-OA-067 using the same reagents as above by reacting the compound OA-4 with 3-ethoxypropylamine.

LC-MS: retention time: 2.85 min (95.85%), m/z: 598.4 (M+H).

$^1$H NMR: (400 MHz, CDCl$_3$): δ 5.321 (m, 1H), 3.648 (s, 3H), 2.907 (m, 1H), 2.086-1.950 (m, 4H), 1.868-1.807 (m, 2H), 1.442-1.320 (m, 3H), 1.182-1.105 (m, 12H), 0.963-0.921 (m, 9H), 0.798 (s, 3H).

BS-OA-042 is prepared according to the process for BS-OA-067 using the same reagents as above by reacting the compound OA-4 with N,N-dimethylpropanediamine.

LC-MS: retention time: 1.59 min (93.40%), m/z: 597.4 (M+H).

$^1$H NMR: (400 MHz, CDCl$_3$): δ 7.697 (s, 1H), 5.355-5.337 (m, 1H), 3.651 (s, 3H), 3.465-3.385 (m, 2H), 2.928-2.884 (m, 1H), 2.511-2.487 (m, 2H), 2.306 (s, 6H), 2.063-1.958 (m, 4H), 1.720-1.636 (m, 8H), 1.561-1.352 (m, 6H), 1.183-1.104 (m, 13H), 0.960-0.929 (m, 9H), 0.799 (s, 3H).

BS-OA-044 is prepared according to the process for BS-OA-067 using the same reagents as above by reacting the compound OA-4 with 3-fluorophenylethylamine.

LC-MS: retention time: 2.86 min (90.22%), m/z: 634.3 (M+H).

$^1$H NMR: (400 MHz, CDCl$_3$): δ 7.325 (m, 1H), 6.994 (m, 2H), 5.355 (m, 1H), 3.673 (s, 3H), 2.877 (m, 3H), 1.440-1.315 (m, 3H), 1.184-1.111 (m, 12H), 0.955-0.922 (m, 9H), 0.790 (s, 3H).

BS-OA-046 is prepared according to the process for BS-OA-067 using the same reagents as above by reacting the compound OA-4 with phenoxyethylamine.

LC-MS: retention time: 2.87 min (92.87%), m/z 632.5 (M+H).

$^1$H NMR: (400 MHz, CDCl$_3$): δ 7.326 (m, 2H), 7.004-6.908 (m, 3H), 5.336 (m, 1H), 3.642 (s, 3H), 2.906 (m, 1H), 2.080-1.888 (m, 3H), 1.766-1.605 (m, 6H), 1.570-1.297 (m, 8H), 1.165-1.092 (m, 11H), 0.937-0.903 (m, 9H), 0.777 (s, 3H).

BS-OA-048 is prepared according to the process for BS-OA-067 using the same reagents as above by reacting the compound OA-4 with cyclopropylmethylamine.

LC-MS: retention time: 2.83 min (95.18%), m/z: 566.4 (M+H).

$^1$H NMR: (400 MHz, CDCl$_3$): δ 5.236 (m, 1H), 3.445 (s, 3H), 3.046 (m, 2H), 2.682 (m, 1H), 1.900-1.707 (m, 3H), 1.603 (d, 1H), 1.502-1.382 (m, 4H), 1.330-1.225 (m, 3H), 1.189-1.108 (m, 3H), 1.978-1.902 (m, 12H), 0.768-0.710 (m, 9H), 0.599 (s, 3H).

BS-OA-052 is prepared according to the process for BS-OA-067 using the same reagents as above by reacting the compound OA-4 with methoxypropylamine.

LC-MS: retention time: 2.76 min (96.04%), m/z: 584.4 (M+H), 606.3 (M+Na).

$^1$H NMR: (400 MHz, CDCl$_3$): δ 5.318 (m, 1H), 3.627 (s, 3H), 3.523 (m, 2H), 3.418-3.361 (m, 5H), 2.891 (m, 1H), 2.075-2.001 (m, 1H), 1.965-1.875 (m, 2H), 1.807 (m, 2H), 1.728-1.682 (m, 2H), 1.644-1.542 (m, 4H), 1.503-1.417 (m, 3H), 1.341 (m, 2H), 1.203-1.081 (m, 12H), 0.941-0.898 (m, 9H), 0.771 (s, 3H).

BS-OA-053 is prepared according to the process for BS-OA-067 using the same reagents as above by reacting the compound OA-4 with ethoxyethylamine.

LC-MS: retention time: 2.77 min (94.49%), m/z: 584.4 (M+H), 606.2 (M+Na).

$^1$H NMR: (400 MHz, CDCl$_3$): δ 5.347 (m, 1H), 3.633 (s, 3H), 3.553-3.454 (m, 6H), 2.068-1.863 (m, 4H), 1.774-1.595 (m, 6H), 1.549-1.270 (m, 7H), 1.239-1.091 (m, 15H), 0.946-0.905 (m, 9H), 0.778 (s, 3H).

BS-OA-054 is prepared according to the process for BS-OA-067 using the same reagents as above by reacting the compound OA-4 with methoxyethylamine.

LC-MS: retention time: 2.78 min (90.27%), m/z: 570.3 (M+H).

$^1$H NMR: (400 MHz, CDC$_{13}$): δ 5.340 (m, 1H), 3.628 (s, 3H), 3.583-3.357 (m, 7H), 2.899 (m, 1H), 2.073-1.920 (m, 4H), 1.544-1.467 (m, 3H), 1.414-1.306 (m, 2H), 1.200-1.085 (m, 12H), 0.941-0.899 (m, 9H), 0.777 (s, 3H).

BS-OA-058 is prepared according to the process for BS-OA-067 using the same reagents as above by reacting the compound OA-4 with 2-isopropoxyethylamine.

LC-MS: retention time: 2.86 min (94.21%), m/z: 598.4 (M+H).

$^1$H NMR: (400 MHz, CDCl$_3$): δ 5.358 (m, 1H), 3.649 (s, 3H), 2.908 (m, 1H), 2.083-1.878 (m, 4H), 1.671-1.632 (m, 3H), 1.417-1.320 (m, 3H), 1.197-1.166 (m, 15H), 1.109 (s, 3H), 0.962-0.925 (m, 9H), 0.793 (s, 3H).

BS-OA-059 is prepared according to the process for BS-OA-067 using the same reagents as above by reacting the compound OA-4 with 4-morpholinylethylamine.

LC-MS: retention time: 3.49 min (90.18%), m/z: 625.4 (M+H).

$^1$H NMR: (400 MHz, CDCl$_3$): δ 5.365 (m, 1H), 3.751 (m, 4H), 3.647 (s, 3H), 3.422 (m, 2H), 2.934 (m, 1H), 2.529 (m, 6H), 2.101-1.885 (m, 4H), 1.785-1.599 (m, 7H), 1.565-1.442 (m, 3H), 1.408-1.324 (m, 3H), 1.224-1.087 (m, 12H), 0.960-0.927 (m, 9H), 0.794 (s, 3H).

BS-OA-062 is prepared according to the process for BS-OA-067 using the same reagents as above by reacting the compound OA-4 with 2-fluorophenylethylamine.

LC-MS: retention time: 2.87 min (92.70%), m/z: 634.3 (M+H).

$^1$H NMR: (400 MHz, CDCl$_3$): δ 7.241 (m, 2H), 7.016 (m, 2H), 5.335 (m, 1H), 3.630 (s, 3H), 2.891 (m, 3H), 2.040-1.929 (m, 2H), 1.858 (d, 2H), 1.722-1.571 (m, 7H), 1.501-1.442 (m, 3H), 1.390-1.341 (m, 3H), 1.154-1.080 (m, 12H), 0.935-0.903 (m, 9H), 0.770 (s, 3H).

BS-OA-064 is prepared according to the process for BS-OA-067 using the same reagents as above by reacting the compound OA-4 with isopropylamine.

LC-MS: retention time: 2.72 min (11.31%, isomer), 2.83 min (82.65%), m/z: 554.4 (M+H), 576.3 (M+Na).

$^1$H NMR: (400 MHz, CDCl$_3$): δ 5.335 (m, 1H), 3.624 (s, 3H), 2.894 (m, 1H), 2.009-1.900 (m, 4H), 1.739-1.611 (m, 6H), 1.540-1.462 (m, 4H), 1.373-1.327 (m, 3H), 1.175-1.035 (m, 18H), 0.945-0.892 (m, 9H), 0.778 (s, 3H).

BS-OA-068 is prepared according to the process for BS-OA-067 using the same reagents as above by reacting the compound OA-4 with propylamine.

LC-MS: retention time: 2.82 min (94.76%), m/z: 554.4 (M+H).

$^1$H NMR: (400 MHz, CDCl$_3$): δ 5.364 (m, 1H), 3.635 (s, 3H), 2.868 (m, 1H), 2.082-1.886 (m, 3H), 1.768-1.656 (m, 6H), 1.383-1.335 (m, 3H), 1.168-1.091 (m, 11H), 0.960-0.902 (m, 11H), 0.785 (s, 3H).

BS-OA-070 is prepared according to the process for BS-OA-067 using the same reagents as above by reacting the compound OA-4 with 3-pentylamine.

LC-MS: 2.72 min (25.86%, isomer), 2.95 min (70.07%), m/z: 582.4 (M+H), 604.3 (M+Na).

$^1$H NMR: (400 MHz, CDCl$_3$): δ 5.343 (m, 1H), 3.625 (s, 3H), 3.475 (m, 1H), 2.879 (m, 1H), 2.001-1.876 (m, 4H), 1.238-1.031 (m, 14H), 0.952-0.893 (m, 9H), 0.766 (s, 3H).

BS-OA-075 is prepared according to the process for BS-OA-067 using the same reagents as above by reacting the compound OA-4 with 1-methoxy-2-propylamine.

LC-MS: retention time: 4.14 min (13.50%, isomer), 4.62 min (86.00%), m/z: 584.4 (M+H).

$^1$H NMR: (400 MHz, CDCl$_3$): δ 5.347 (m, 1H), 3.630 (s, 3H), 3.372 (m, 5H), 2.870 (m, 1H), 2.075-1.916 (m, 4H), 1.547-1.451 (m, 3H), 1.411-1.325 (m, 3H), 1.204-1.083 (m, 12H), 0.943-0.895 (m, 9H), 0.779 (s, 3H).

BS-OA-078 is prepared according to the process for BS-OA-067 using the same reagents as above by reacting the compound OA-4 with 1-(3-aminopropyl)-4-methylpiperazine.

LC-MS: retention time: 2.30 min (90.63%), m/z: 652.5 (M+H).

$^1$H NMR: (400 MHz, CDCl$_3$): δ 6.447-6.443 (m, 1H), 5.328-5.295 (m, 1H), 3.630 (s, 3H), 3.565-3.517 (m, 1H), 3.271-3.236 (m, 1H), 2.907-2.863 (m, 1H), 2.592-2.400 (m, 7H), 2.271 (s, 4H), 2.069-1.923 (m, 4H), 1.767-1.589 (m, 8H), 1.545-1.408 (m, 4H), 1.365-1.297 (m, 3H), 1.207-1.043 (m, 14H), 0.946 (s, 3H), 0.919 (s, 3H), 0.878 (s, 3H), 0.795 (s, 3H).

BS-OA-082 is prepared according to the process for BS-OA-067 using the same reagents as above by reacting the compound OA-4 with furan-2-ylmethylamine.

LC-MS: retention time: 2.72 min (91.18%), m/z: 592.3 (M+H), 614.3 (M+Na).

$^1$H NMR: (400 MHz, CDCl$_3$): δ 7.401 (m, 1H), 6.362-6.268 (m, 2H), 5.350 (m, 1H), 3.648 (s, 3H), 2.921 (m, 1H), 2.059-1.920 (m, 3H), 1.541-1.471 (m, 3H), 1.407-1.349 (m, 3H), 1.185-1.112 (m, 12H), 0.963-0.916 (m, 9H), 0.795 (s, 3H).

BS-OA-085 is prepared according to the process for BS-OA-067 using the same reagents as above by reacting the compound OA-4 with 5-methylfurfurylamine.

LC-MS: retention time: 2.80 min (90.36%), m/z: 606.4 (M+H).

$^1$H NMR: (400 MHz, CDCl$_3$): δ 6.122 (s, 1H), 5.906 (s, 1H), 5.322 (s, 1H), 3.629 (s, 3H), 2.891 (m, 1H), 2.285 (s, 3H), 2.064-1.873 (m, 4H), 1.765 (d, 1H), 1.502-1.448 (m, 3H), 1.410-1.327 (m, 3H), 1.161-1.054 (m, 14H), 0.941-0.895 (m, 9H), 0.773 (s, 3H).

BS-OA-086 is prepared according to the process for BS-OA-067 using the same reagents as above by reacting the compound OA-4 with 3-anisidine.

LC-MS: retention time: 4.40 min (28.43%, isomer), 4.86 min (66.82%), m/z: 618.5 (M+H).

$^1$H NMR: (400 MHz, CDCl$_3$): δ 7.219 (m, 1H), 6.971 (m, 2H), 6.708 (m, 1H), 5.390 (m, 1H), 3.829 (s, 3H), 3.658 (s, 3H), 2.936 (m, 1H), 2.183 (d, 1H), 1.732-1.642 (m, 5H), 1.595-1.500 (m, 4H), 1.464-1.362 (m, 3H), 1.219-1.131 (m, 12H), 0.960-0.927 (m, 9H), 0.823 (s, 3H).

BS-OA-088 is prepared according to the process for BS-OA-067 using the same reagents as above by reacting the compound OA-4 with 2-thiopheneethylamine.

LC-MS: retention time: 2.85 min (91.50%), m/z: 622.4 (M+H).

$^1$H NMR: (400 MHz, CDCl$_3$): δ 7.190 (dd, J=5.2 Hz, 1H), 6.974 (dd, J=5.2 Hz, 1H), 6.841 (m, 1H), 5.311 (m, 1H), 3.628 (s, 3H), 2.862 (m, 1H), 2.031-1.929 (m, 2H), 1.849 (d, 1H), 1.733-1.590 (m, 8H), 1.500-1.445 (m, 3H), 1.410-1.331 (m, 3H), 1.163-1.088 (m, 12H), 0.935-0.903 (m, 9H), 0.769 (s, 3H).

EXAMPLE 2

Synthesis of Compound BS-OA-105

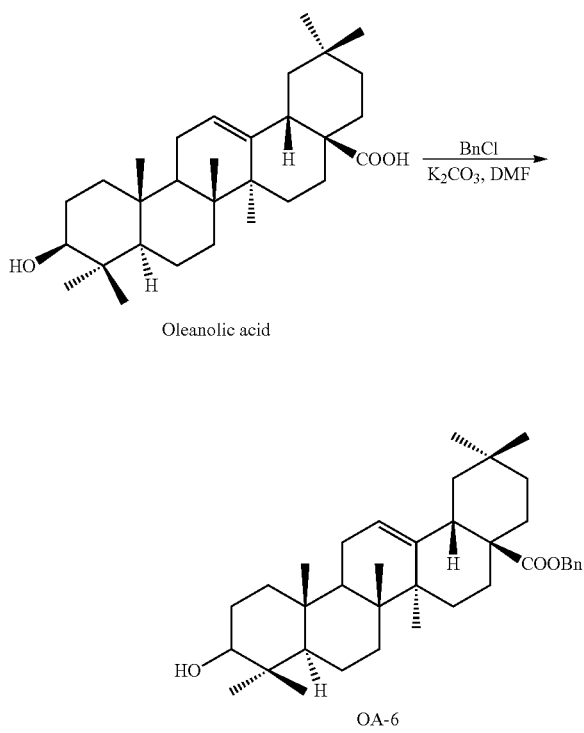

Oleanolic acid

OA-6 wherein BnCl is benzyl chloride.

To N,N-dimethylformamide (300 mL) are added oleanolic acid (20 g, 43.8 mmol) and potassium carbonate (6.7 g, 48.2 mmol), followed by the addition of benzyl chloride (6.1 g, 48.2 mmol) all at once. The reaction solution is heated up to 100° C. and stirred overnight. After the reaction is completed, the solvent is rotavapped off and water (100 mL) is added. Dichloromethane (200 mL*3) is used for extraction. The organic phases are combined, dried with anhydrous sodium sulfate, and solvents are rotavapped off to give a crude product OA-6 (21.5 g, 90%) as a solid.

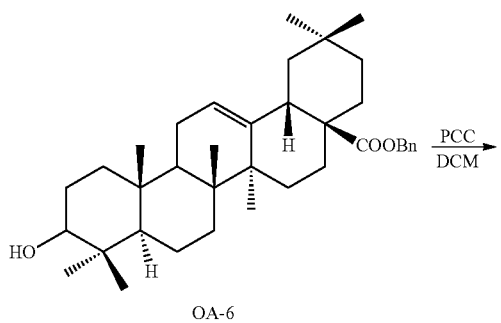

OA-6

-continued

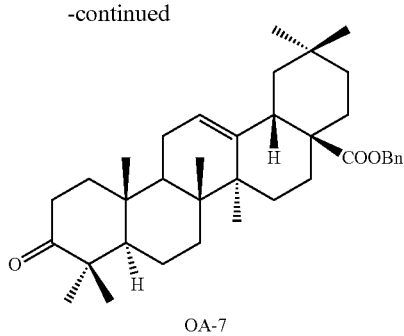
OA-7

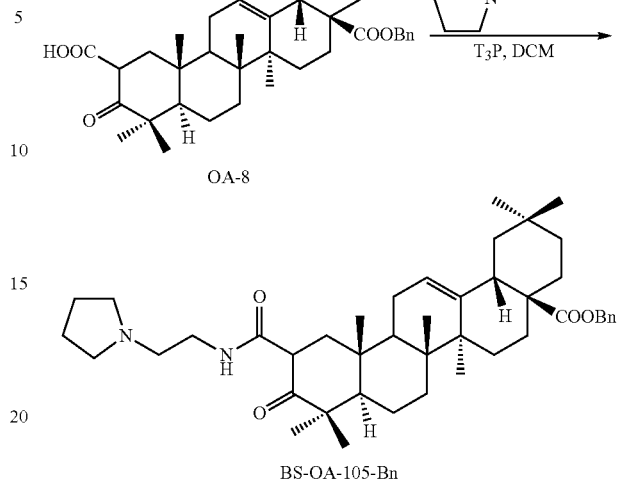
OA-8

To dichloromethane (500 mL) are added OA-6 (21.5 g, 39.38 mmol) and pyridinium chlorochromate (10.18 g, 47.25 mol), and the reaction is carried out with stirring overnight under room temperature. When the reaction is completed, the reaction solution is filtered. The crude product resulted from rotavapping the filtrate is separated and purified via a silica-gel column using petroleum ether: ethyl acetate: dichloromethane (100:1:1~20:1:1~10:1:1) to give compound OA-7 (17 g, 79.36%) as a white solid.

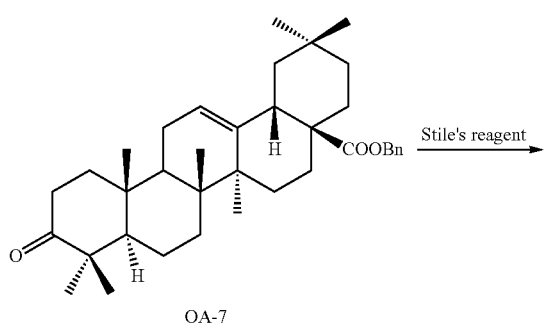
OA-7

To 10 mL dichloromethane are added the compound OA-8 (1000 mg, 1.70 mmol) and pyrrolidineethylamine (194 mg, 1.70 mmol), and then tripropylphosphoric anhydride (80.4 mg, 0.253 mmol) is added. The reaction solution is agitated for 16 hours under 30° C. When the reaction is completed, the reaction solution is concentrated, and the resulted oily compound is separated and purified via a silica-gel column using petroleum ether: ethyl acetate (10:1~1:1) to give compound BS-OA-105-Bn (400 mg, 34.42%) as a yellow solid.

BS-OA-105-Bn

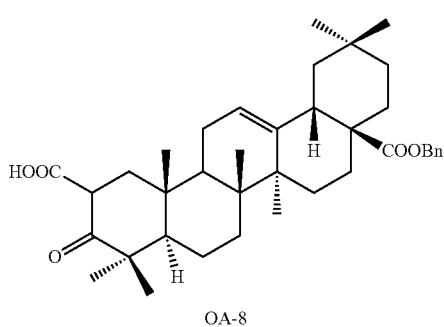
OA-8

Under nitrogen protection, a mixed solution of the compound OA-7 (15 g, 27.57 mmol) and Stile's Reagent (117.18 mL) is heated up to 110° C. After the reaction solution is stirred for 1.5 hours, hydrochloric acid (5%) is injected into the reaction solution, which is then extracted with ethyl acetate (500 mL*3). The organic phase is dried with anhydrous sodium sulfate and the crude product after concentration is separated and purified via a silica-gel column using petroleum ether: ethyl acetate (1:0~100:1~80:1) to give compound OA-8 (12 g, 74.02%) as a white solid.

BS-OA-105

The compound BS-OA-105-Bn (400 mg, 0.58 mmol) is dissolved in methanol (20 mL), to which Pd/C (80 mg, cat.) is added. Under hydrogen gas (1 atm) and the reaction temperature controlled at 30° C., the reaction solution is stirred for 2 hours. After completion of the reaction, the reaction solution is filtered. Crude product resulted from rotavapping and concentrating the filtrate is separated and purified via preparative thin layer chromatography to give compound BS-OA-105 (36.7 mg, 10.6%) as a white solid.

LC-MS: retention time: 2.92 min (99.23%), m/z: 595.4 (M+H).

$^1$H NMR: (400 MHz, CDCl$_3$): δ 11.467-11.396 (m, 1H), 7.094 (m, 1H), 5.321-5.300 (m, 1H), 3.622-3.574 (m, 1H), 3.456-3.409 (m, 1H), 2.940-2.897 (m, 7H), 2.121-2.014 (m, 3H), 1.981-1.869 (m, 5H), 1.819-1.705 (m, 3H), 1.670-1.592 (m, 3H), 1.532-1.458 (m, 3H), 1.395-1.330 (m, 3H), 1.163-1.073 (m, 13H), 0.982 (m, 9H), 0.917 (s, 3H).

BS-OA-106 is prepared according to the process for BS-OA-105 using the same reagents as above by reacting the compound OA-8 with N,N-diethylethylenediamine.

LC-MS: retention time: 2.96 min (98.54%), m/z: 597.4 (M+H).

$^1$H NMR: (400 MHz, CDCl$_3$): δ 6.647 (m, 1H), 5.242 (m, 1H), 3.428-3.347 (m, 2H), 2.844-2.658 (m, 7H), 2.000-1.939 (m, 3H), 1.880-1.650 (m, 4H), 1.617-1.551 (m, 3H), 1.469-1.393 (m, 3H), 1.333-1.264 (m, 4H), 1.095-1.010 (m, 18H), 0.907-0.854 (m, 9H), 0.848 (s, 3H).

BS-OA-107 is prepared according to the process for BS-OA-105 using the same reagents as above by reacting the compound OA-8 with 1-pyrrolidinepropylamine.

LC-MS: retention time: 2.97 min (100.0%), m/z: 609.4 (M+H).

$^1$H NMR: (400 MHz, CDCl$_3$): δ 7.614 (m, 1H), 5.213 (m, 1H), 3.249-3.202 (m, 1H), 3.187-3.072 (m, 1H), 2.785-2.751 (m, 1H), 2.528-2.508 (m, 2H), 2.434-2.400 (m, 4H), 2.080-2.022 (m, 2H), 1.917-1.874 (m, 2H), 1.673-1.544 (m, 10H), 1.494-1.420 (m, 4H), 1.332-1.278 (m, 3H), 1.099-0.977 (m, 13H), 0.868-0.842 (m, 9H), 0.786 (s, 3H).

BS-OA-108 is prepared according to the process for BS-OA-105 using the same reagents as above by reacting the compound OA-8 with N,N-diethylpropylenediamine.

LC-MS: retention time: 2.98 min (99.52%), m/z: 611.4 (M+H).

$^1$H NMR: (400 MHz, CDCl$_3$): δ 6.982 (m, 1H), 5.297 (m, 1H), 3.419-3.312 (m, 2H), 2.895-2.730 (m, 7H), 2.066-1.904 (m, 4H), 1.871-1.737 (m, 6H), 1.688-1.579 (m, 3H), 1.520-1.462 (m, 3H), 1.389-1.350 (m, 3H), 1.160-1.075 (m, 19H), 0.964-0.912 (m, 9H), 0.820 (s, 3H).

BS-OA-109 is prepared according to the process for BS-OA-105 using the same reagents as above by reacting the compound OA-8 with N,N-dimethylpropylenediamine.

LC-MS: retention time: 2.87 min (99.20%), m/z: 583.4 (M+H).

$^1$H NMR: (400 MHz, CDCl$_3$): δ 8.407-8.240 (m, 1H), 6.867 (m, 1H), 5.263-5.231 (m, 1H), 3.318-3.233 (m, 3H), 2.833-2.803 (m, 1H), 2.594-2.513 (m, 2H), 2.447-2.335 (m, 6H), 1.958-1.870 (m, 4H), 1.837-1.669 (m, 5H), 1.624-1.561 (m, 3H), 1.533-1.487 (m, 3H), 1.456-1.295 (m, 3H), 1.095-1.014 (m, 13H), 0.894-0.862 (m, 9H), 0.765 (s, 3H).

BS-OA-110 is prepared according to the process for BS-OA-105 using the same reagents as above by reacting the compound OA-8 with 1-(3-aminopropyl)-4-methylpiperazine.

LC-MS: retention time: 2.89 min (98.04%), m/z: 638.5 (M+H).

$^1$H NMR: (400 MHz, CDCl$_3$): δ 9.023-8.885 (m, 1H), 6.242 (m, 1H), 5.319 (m, 1H), 3.469-3.434 (m, 1H), 3.264-3.237 (m, 1H), 2.883-2.858 (m, 1H), 2.591-2.494 (m, 9H), 2.011-1.898 (m, 4H), 1.758-1.727 (m, 5H), 1.661-1.532 (m, 4H), 1.493-1.466 (m, 3H), 1.365-1.306 (m, 3H), 1.158-1.074 (m, 13H), 0.927-0.887 (m, 9H), 0.833 (s, 3H).

EXAMPLE 3

Evaluation of the 2-Substituted Oleanolic Acid Derivatives of the Present Invention for their Anti-Leukemia Activities (1) Experimental Materials Leukemia cell lines: leukemia cell lines: K562/adr (drug-resistant, chronic myeloid leukemia, CML), NB4 (acute promyelocytic leukemia, AML), Kasumi-1 (acute myeloid leukemia M2 type, AML-M2), Jurkat (acute lymphoblastic leukemia, ALL), all of which are donated by Cancer Research Institute of Zhejiang University, China; and H9 (acute lymphoblastic leukemia, ALL), which is purchased from China Center for Type Culture Collection (CCTCC).

Reagents: The standard sample of oleanolic acid (OA) is purchased from Hua Kang Pharmaceutical Raw Material Factory, Shifang City, Sichuan, China, and the 2-substituted oleanolic acid derivatives are obtained according to the present invention.

Main apparatuses: cell incubator (model: Thermo Scientific 3111) and microplate absorbance reader (model: Bio-Rad iMark).

(2) Experimental Method

Obtaining 6000 well-growing leukemia cells and inoculating them into wells of a 96-well cell culture plate. The culture medium is the 1640 cell culture medium containing 10% fetal bovine serum. After adding the 2-substituted oleanolic acid derivatives of different concentrations and mixing uniformly, placing the plate in a carbon dioxide cell incubator (5% CO$_2$) at 37° C. and incubated for 72 hours. Then the relative number of viable cells is determined by MTT method. In this experiment, cell proliferation inhibition rate in control group (not treated with any compound) is set as 0%. Based on the relative number of living cells, the half maximum inhibitory concentration for leukemia cells at 72 hours (IC$_{50}$ value of 72 hours, μg/mL) and the leukemia cell proliferation inhibition rate (IR) by the 16 μg/mL compound at 72 hours are calculated.

(3) Experimental Results

The experimental results are shown in table 1.

Table 1 shows that the 2-substituted oleanolic acid derivatives of the present invention can induce cell death of human chronic myeloid leukemia cells, acute myeloid leukemia cells and acute lymphocytic leukemia cells, and inhibit the growth of these leukemia cells. Specifically, as compared with oleanolic acid per se, the inventive 2-substituted oleanolic acid derivatives BS-OA-005, BS-OA-012, BS-OA-016, BS-OA-035, BS-OA-042 and BS-OA-078 improve the inhibition rate of K562/adr cell line by more than 3-fold and improve the inhibition rate of Jurkat cell line by more than 10-fold; BS-OA-005, BS-OA-012, BS-OA-016 and BS-OA-035 improve the inhibition rate of Kasumi-1 cell line by more than 5-fold; BS-OA-004, BS-OA-005, BS-OA-012, BS-OA-016, BS-OA-035 and BS-OA-042 improve the inhibition rate of NB4 cell line by more than 5-fold; BS-OA-016 and BS-OA-035 improve inhibition rate on the H9 cell line by more than 4-fold.

TABLE 1

Determination of the inhibiting concentrations of the 2-substituted oleanolic acid derivatives on leukemia cell growth (72 h, $IC_{50}$ value and IR value, μg/mL).

| Compounds | K562/adr | | Kasumi-1 | | NB4 | |
|---|---|---|---|---|---|---|
| | $IC_{50}$ | IR | $IC_{50}$ | IR | $IC_{50}$ | IR |
| OA | >16 | 26.5% | >16 | 17.2% | >16 | 17.2% |
| BS-OA-004 | 2.41 | 98.3% | 6.5 | 99.6% | 2.84 | 100.0% |
| BS-OA-005 | 1.16 | 100.0% | 3.98 | 99.8% | 2.73 | 100.0% |
| BS-OA-008 | 8 | 70.1% | >16 | 6.7% | >16 | 6.3% |
| BS-OA-012 | 1.09 | 99.0% | 3.18 | 99.3% | 2.79 | 99.2% |
| BS-OA-016 | 0.52 | 97.8% | 3.76 | 99.1% | 2.94 | 99.8% |
| BS-OA-027 | 3.7 | 82.6% | 12.39 | 72.2% | 4.57 | 93.8% |
| BS-OA-031 | 12.05 | 62.2% | >16 | 10.0% | >16 | −0.9% |
| BS-OA-032 | 12.88 | 63.7% | 16 | 48.6% | 9.82 | 85.2% |
| BS-OA-034 | >16 | 25.3% | >16 | 22.6% | >16 | 22.3% |
| BS-OA-035 | 0.68 | 99.6% | 3.95 | 97.0% | 2.96 | 99.8% |
| BS-OA-037 | 1.57 | 97.6% | 13.47 | 63.7% | 4.59 | 97.6% |
| BS-OA-042 | 0.64 | 98.4% | 4.1 | 99.1% | 2.63 | 100.0% |
| BS-OA-048 | >16 | 21.4% | >16 | 0.2% | >16 | 11.0% |
| BS-OA-052 | 12.29 | 64.0% | >16 | 19.0% | 16 | 46.7% |
| BS-OA-053 | 10.75 | 60.9% | >16 | 23.2% | 10.69 | 71.3% |
| BS-OA-059 | 8.87 | 80.5% | 16 | 48.7% | 9.74 | 86.7% |
| BS-OA-078 | 0.89 | 99.1% | 5.67 | 97.9% | 4.59 | 100.0% |
| BS-OA-105 | 6.52 | 85.0% | >16 | 36.6% | 10.59 | 74.7% |
| BS-OA-106 | 4.12 | 98.2% | >16 | 43.0% | 7.32 | 86.6% |
| BS-OA-108 | 4.83 | 96.1% | 10.16 | 74.5% | 6.86 | 92.4% |
| BS-OA-109 | 6.8 | 86.2% | >16 | 36.2% | 10.77 | 76.6% |
| BS-OA-110 | 8.79 | 81.9% | >16 | 41.7% | 8.95 | 78.8% |

| Compounds | H9 | | Jurkat | |
|---|---|---|---|---|
| | $IC_{50}$ | IR | $IC_{50}$ | IR |
| OA | >16 | 22.8% | >16 | 9.4% |
| BS-OA-004 | 5.67 | 98.2% | 6.15 | 97.7% |
| BS-OA-005 | 3.16 | 96.2% | 2.33 | 98.1% |
| BS-OA-008 | >16 | 39.8% | >16 | −33.8% |
| BS-OA-012 | 3.05 | 95.0% | 2.26 | 97.0% |
| BS-OA-016 | 2.96 | 95.4% | 2.38 | 95.1% |
| BS-OA-027 | 7.72 | 92.5% | 9.85 | 83.4% |
| BS-OA-031 | >16 | 31.9% | >16 | −28.5% |
| BS-OA-032 | 13.6 | 62.3% | 10.84 | 75.4% |
| BS-OA-034 | >16 | 22.1% | >16 | −19.6% |
| BS-OA-035 | 2.67 | 97.5% | 1.67 | 96.6% |
| BS-OA-037 | 8.73 | 95.8% | 11.46 | 80.4% |
| BS-OA-042 | 3.12 | 95.9% | 2.43 | 99.0% |
| BS-OA-048 | >16 | 28.9% | >16 | −21.2% |
| BS-OA-052 | >16 | 38.0% | >16 | −5.0% |
| BS-OA-053 | 15.53 | 54.6% | >16 | 13.0% |
| BS-OA-059 | 12.73 | 67.7% | >16 | 23.8% |
| BS-OA-078 | 4.33 | 97.5% | 2.5 | 98.3% |
| BS-OA-105 | >16 | 31.5% | >16 | 37.5% |
| BS-OA-106 | >16 | 44.6% | >16 | 43.2% |
| BS-OA-108 | 15.3 | 57.7% | 12.61 | 66.5% |
| BS-OA-109 | >16 | 39.4% | >16 | 32.3% |
| BS-OA-110 | >16 | 37.9% | 18.36 | 45.5% |

EXAMPLE 4

Evaluation of the Activities Against Human Multiple Myeloma Cells by the 2-Substituted Oleanolic Acid Derivatives of the Present Invention (1) Experimental Materials Multiple myeloma cell lines: RPMI8226 (multiple myeloma), purchased from Fuxiang Bio-tech Co. Ltd., Shanghai, China.

Reagents: the same as in Example 3.

Main apparatuses: cell incubator (model: Thermo Scientific 3111) and a microplate absorbance reader (model: Bio-Rad iMark).

(2) Experimental Method

Obtaining 6000 well-growing cells as above and inoculating them into wells of a 96-well cell culture plate. The culture medium is the 1640 cell culture medium containing 10% fetal bovine serum. After adding the 2-substituted oleanolic acid derivatives of different concentrations and mixing uniformly, placing the plate in a carbon dioxide cell incubator (5% $CO_2$) at 37° C. and incubated for 72 hours. Then the relative number of viable cells is determined by MTT method. In this experiment, cell proliferation inhibition rate in control group (not treated with any compound) is set as 0%. Based on the relative number of living cells, the half maximum inhibitory concentration for the leukemia cells at 72 hours ($IC_{50}$ value of 72 hours, μg/mL) and the tumor cell proliferation inhibition rate (IR) by the 16 μg/mL compound at 72 hours are calculated.

(3) Experimental Results

The experimental results are shown in table 2.

Table 2 shows that the 2-substituted oleanolic acid derivatives of the present invention can induce the death of human myeloma cells and inhibit the growth of these tumor cells. Specifically, as compared with oleanolic acid per se, the inventive 2-substituted oleanolic acid derivatives BS-OA-005, BS-OA-012, BS-OA-035, BS-OA-042 and BS-OA-078 improve the inhibition rate of RPMI8226 cell line by more than 44-fold.

EXAMPLE 5

Evaluation of the Effect of the 2-Substituted Oleanolic Acid Derivatives of the Present Invention Against Human Solid Tumor (1) Experimental Materials Human Solid Tumor Cell Lines:

Hep-2 (laryngeal carcinoma), A549 (human lung cancer), CaES-17 (esophageal cancer cell), PC-3 (prostate cancer), CNE (nasopharyngeal carcinoma cell), and SK-OV-3 (ovarian cancer cell), all of which are purchased from China Center For Type Culture Collection; RKO (human colon adenocarcinoma cell), MGC 803 (human gastric cancer cell), MG63 (osteosarcoma) and U87 MG (malignant glioma cell), all of which are purchased from Fuxiang Bio-tech Co. Ltd., Shanghai, China; PANC-1 (pancreatic cancer), Hep G2 (human liver cancer cell), Becap3 (human breast cancer cell), and Hela (human cervical cancer cell), all of which are donated by Cancer Research Institute of Zhejiang University, China.

Reagents: the same as in Example 4.

Main apparatuses: cell incubator (model: Thermo Scientific 3111) and a microplate absorbance reader (model: Bio-Rad iMark).

(2) Experimental Method

Obtaining 4000 well-growing human solid tumor cells and inoculating them into wells of a 96-well cell culture plate. The culture medium is DMEM High Glucose cell culture medium containing 10% fetal bovine serum. The plate is placed in a carbon dioxide cell incubator (5% $CO_2$) at 37° C. for 24 hours. After adding the 2-substituted oleanolic acid derivatives of different concentrations and mixing uniformly, the plate is placed in a carbon dioxide cell incubator (5% $CO_2$) at 37° C. and incubated for 72 hours. Then the relative number of the living cells is determined by MTT method. In this experiment, the cell proliferation inhibition rate in control group (not treated with any compound) is set as 0%. Based on the relative number of living cells, the half maximum inhibiting concentration for the leukemia cells at 72 hours (IC$_{50}$ value of 72 hours, μg/mL) and the solid tumor cell proliferation inhibition rate (IR) by the 16 μg/mL compound at 72 hours are calculated.

(3) Experimental Results are Shown in Table 2.

Table 2 shows that the 2-substituted oleanolic acid derivatives of the present invention can induce cell death of human solid tumor and inhibit the growth of these tumor cells. Specifically, as compared with oleanolic acid per se, the inventive 2-substituted oleanolic acid derivatives BS-OA-005, BS-OA-016, BS-OA-035 and BS-OA-042 improve the inhibition rate of A549 and RKO cell lines by more than 19-fold and 6-fold, respectively; BS-OA-005, BS-OA-012, BS-OA-016 and BS-OA-035 improve the inhibition rate of PANC-1 cell line by more than 11-fold; BS-OA-012 and BS-OA-042 improve the inhibition rate of Becap37 cell line by more than 4-fold; BS-OA-005, BS-OA-012, BS-OA-035 and BS-OA-042 improve the inhibition rate of MG-63 and CNE cell lines by more than 3-fold and 2-fold, respectively; BS-OA-016, BS-OA-035 and BS-OA-042 improve the inhibition rate of Hela cell line by more than 4-fold; BS-OA-005, BS-OA-012, BS-OA-016, BS-OA-035 and BS-OA-042 improve the inhibition rate of U87 MG, PC-3, MGC 803 and Hep-2 cell lines by more than 4-fold, 3-fold, 5-fold and 9-fold, respectively; BS-OA-012, BS-OA-035 and BS-OA-042 improve the inhibition rate of CaES-17 and SK-OV-3 cell lines by more than 3-fold and 11-fold, respectively; as to the Hep G2 cell line, oleanolic acid per se does not exhibit obvious proliferation inhibition effect on this cell line, but the oleanolic acid derivatives of the present invention all exhibit good cell proliferation inhibition effect, wherein BS-OA-005, BS-OA-012, BS-OA-016, BS-OA-035 and BS-OA-042 exhibit particularly remarkable effect, all showing an inhibition rate of more than 96%.

TABLE 2

Determination of the inhibiting concentrations of the 2-substituted oleanolic acid derivatives on multiple myeloma and human solid tumor cell growth (72 h, IC$_{50}$ value and IR value, μg/mL).

| Compounds | RPMI8226 | | A549 | | PANC-1 | |
|---|---|---|---|---|---|---|
| | IC$_{50}$ | IR | IC$_{50}$ | IR | IC$_{50}$ | IR |
| OA | >16 | 2.2% | >16 | 5.0% | >16 | 8.5% |
| BS-OA-004 | 2.08 | 98.3% | 7.7 | 92.0% | 8.77 | 94.1% |
| BS-OA-005 | 0.69 | 99.2% | 2.19 | 96.8% | 4.54 | 97.8% |
| BS-OA-008 | >16 | 30.0% | >16 | 3.4% | >16 | −4.6% |
| BS-OA-012 | 0.74 | 99.0% | 2.83 | 97.4% | 4.73 | 100.0% |
| BS-OA-016 | 1.15 | 99.0% | 2.45 | 96.8% | 4.38 | 98.5% |
| BS-OA-027 | 6.1 | 86.5% | >16 | 45.6% | >16 | 36.9% |
| BS-OA-031 | >16 | 4.4% | >16 | −6.3% | >16 | −1.4% |
| BS-OA-032 | >16 | 30.3% | >16 | −6.6% | >16 | 14.5% |
| BS-OA-034 | >16 | 15.5% | >16 | 5.3% | >16 | −9.9% |
| BS-OA-035 | 0.61 | 99.1% | 2.02 | 97.3% | 4.89 | 99.8% |
| BS-OA-037 | 2.43 | 99.1% | 10.4 | 82.0% | >16 | 11.3% |
| BS-OA-042 | 0.68 | 98.9% | 2.06 | 96.9% | 5.02 | 99.4% |
| BS-OA-048 | >16 | 4.9% | >16 | −3.8% | >16 | −17.8% |
| BS-OA-052 | >16 | 25.2% | >16 | 3.1% | >16 | 8.4% |
| BS-OA-053 | >16 | 29.5% | >16 | 2.0% | >16 | −3.3% |
| BS-OA-059 | 7.18 | 96.6% | >16 | 11.8% | >16 | 10.4% |
| BS-OA-078 | 0.74 | 99.1% | 3.58 | 97.6% | 9.69 | 100.0% |
| BS-OA-105 | 10.54 | 81.8% | >16 | 24.0% | >16 | 16.9% |
| BS-OA-106 | 12.25 | 68.3% | >16 | 31.5% | >16 | 16.9% |
| BS-OA-108 | 6.4 | 97.3% | >16 | 27.5% | >16 | 21.6% |
| BS-OA-109 | 6.21 | 96.0% | >16 | 7.5% | >16 | 12.9% |
| BS-OA-110 | 8.58 | 96.7% | >16 | 4.0% | >16 | 13.1% |

| Compounds | Becap37 | | MG-63 | | Hep G2 | | RKO | |
|---|---|---|---|---|---|---|---|---|
| | IC$_{50}$ | IR | IC$_{50}$ | IR | IC$_{50}$ | IR | IC$_{50}$ | IR |
| OA | >16 | 23.4% | >16 | 29.2% | >16 | −18.5% | >16 | 14.3% |
| BS-OA-004 | >16 | 43.9% | 8.37 | 99.0% | 4.89 | 100.0% | 7.4 | 98.9% |
| BS-OA-005 | 5.68 | 98.6% | 2.31 | 99.7% | 2.53 | 99.7% | 3.19 | 98.7% |
| BS-OA-008 | >16 | 2.3% | >16 | −12.1% | >16 | 8.1% | >16 | −18.6% |
| BS-OA-012 | 4.42 | 98.4% | 2.2 | 100.0% | 2.36 | 99.9% | 2 | 97.6% |
| BS-OA-016 | 5.12 | 99.5% | 4.35 | 100.0% | 2.58 | 96.9% | 3.33 | 99.4% |
| BS-OA-027 | >16 | 34.3% | >16 | 25.4% | 15.59 | 51.4% | 16 | 46.8% |
| BS-OA-031 | >16 | −5.8% | >16 | −1.3% | >16 | 6.7% | >16 | −12.1% |
| BS-OA-032 | >16 | 4.1% | >16 | 4.7% | >16 | 23.7% | >16 | −5.3% |
| BS-OA-034 | >16 | −6.7% | >16 | −5.4% | >16 | 8.9% | >16 | −41.0% |
| BS-OA-035 | 5.2 | 98.6% | 1.62 | 100.0% | 1.94 | 97.9% | 2.39 | 97.2% |
| BS-OA-037 | >16 | 8.4% | 12.46 | 64.6% | 8.68 | 95.7% | 14.38 | 62.6% |
| BS-OA-042 | 4.32 | 98.7% | 2.72 | 98.2% | 2.36 | 99.8% | 3.29 | 100.0% |
| BS-OA-048 | >16 | −8.4% | >16 | −20.3% | >16 | 7.4% | >16 | −33.4% |
| BS-OA-052 | >16 | −12.0% | >16 | −33.5% | >16 | 10.0% | >16 | −48.6% |
| BS-OA-053 | >16 | −10.2% | >16 | −32.5% | >16 | 6.8% | >16 | −55.6% |
| BS-OA-059 | >16 | 4.7% | >16 | 27.0% | >16 | 0.6% | >16 | 1.8% |
| BS-OA-078 | 6.23 | 98.1% | 5.7 | 100.0% | 4.77 | 99.7% | 3.91 | 97.5% |
| BS-OA-105 | >16 | 43.7% | 12.57 | 54.6% | >16 | 29.5% | >16 | 8.6% |
| BS-OA-106 | >16 | 27.5% | >16 | 4.9% | >16 | 33.6% | >16 | 5.3% |
| BS-OA-108 | >16 | 38.4% | >16 | 47.4% | >16 | 42.3% | 14.32 | 63.2% |

TABLE 2-continued

Determination of the inhibiting concentrations of the 2-substituted oleanolic acid derivatives on multiple myeloma and human solid tumor cell growth (72 h, IC$_{50}$ value and IR value, μg/mL).

| | | | | | | | | |
|---|---|---|---|---|---|---|---|---|
| BS-OA-109 | >16 | 19.7% | >16 | 18.9% | >16 | 32.1% | >16 | −4.9% |
| BS-OA-110 | >16 | 22.2% | >16 | 29.5% | >16 | 29.5% | >16 | −19.1% |

| | U87 MG | | Hela | | CaES-17 | | CNE | |
|---|---|---|---|---|---|---|---|---|
| Compounds | IC$_{50}$ | IR | IC$_{50}$ | IR | IC$_{50}$ | IR | IC$_{50}$ | IR |
| OA | >16 | 21.8% | >16 | 22.9% | >16 | 27.4% | >16 | 33.9% |
| BS-OA-004 | 10.02 | 98.0% | 9.28 | 99.4% | 8.88 | 81.2% | 8.46 | 97.3% |
| BS-OA-005 | 2.5 | 100.0% | 4.05 | 98.6% | 3.34 | 98.9% | 3.65 | 98.6% |
| BS-OA-008 | >16 | 30.1% | >16 | 0.5% | >16 | −12.7% | >16 | 15.1% |
| BS-OA-012 | 2.56 | 98.5% | 4.19 | 96.9% | 1.91 | 99.1% | 3.74 | 98.8% |
| BS-OA-016 | 2.45 | 100.0% | 3.78 | 98.0% | 3.93 | 99.4% | 4.07 | 99.4% |
| BS-OA-027 | 16 | 48.7% | 10.75 | 62.0% | 16.99 | 49.5% | 15.6 | 51.3% |
| BS-OA-031 | >16 | 5.3% | >16 | 2.5% | >16 | −4.7% | >16 | 15.8% |
| BS-OA-032 | >16 | 30.4% | 15.85 | 57.0% | >16 | 22.0% | >16 | 23.6% |
| BS-OA-034 | >16 | 18.2% | >16 | 0.6% | >16 | −6.7% | >16 | 16.7% |
| BS-OA-035 | 2.7 | 97.1% | 3.11 | 98.1% | 2.74 | 98.0% | 3.64 | 99.0% |
| BS-OA-037 | 11.13 | 92.6% | 11.04 | 93.6% | 11.58 | 82.3% | 15.49 | 52.6% |
| BS-OA-042 | 2.54 | 98.6% | 3.47 | 98.9% | 2.97 | 98.1% | 3.89 | 99.5% |
| BS-OA-048 | >16 | 5.6% | >16 | 2.4% | >16 | −18.6% | >16 | 21.9% |
| BS-OA-052 | >16 | 10.9% | >16 | 25.6% | >16 | −8.0% | >16 | 9.9% |
| BS-OA-053 | >16 | 20.1% | >16 | 27.5% | >16 | −13.1% | >16 | 9.9% |
| BS-OA-059 | >16 | 30.6% | 16 | 51.8% | >16 | 34.0% | >16 | 20.6% |
| BS-OA-078 | 3 | 98.6% | 4.54 | 99.4% | 3.61 | 99.4% | 5.01 | 99.7% |
| BS-OA-105 | 2.31 | 61.7% | 7.29 | 68.1% | 18.86 | 45.0% | 10.57 | 54.5% |
| BS-OA-106 | >16 | 7.2% | >16 | 34.6% | >16 | 10.0% | >16 | 44.3% |
| BS-OA-108 | >16 | 18.5% | >16 | 43.0% | >16 | 32.0% | >16 | 42.7% |
| BS-OA-109 | >16 | −3.8% | >16 | 23.6% | >16 | 4.1% | >16 | 36.5% |
| BS-OA-110 | >16 | −12.6% | >16 | 26.1% | >16 | −1.0% | >16 | 30.1% |

| | Hep-2 | | MGC 803 | | PC-3 | | SK-OV-3 | |
|---|---|---|---|---|---|---|---|---|
| Compounds | IC$_{50}$ | IR | IC$_{50}$ | IR | IC$_{50}$ | IR | IC$_{50}$ | IR |
| OA | >16 | 9.8% | >16 | 19.7% | >16 | 29.1% | >16 | 8.3% |
| BS-OA-004 | 10.07 | 85.5% | 7.32 | 98.1% | 9.91 | 89.8% | 9.14 | 94.9% |
| BS-OA-005 | 5.09 | 99.2% | 2.7 | 99.3% | 5.11 | 99.2% | 4.23 | 98.3% |
| BS-OA-008 | >16 | 3.5% | >16 | −12.4% | >16 | 12.0% | >16 | 14.3% |
| BS-OA-012 | 5.5 | 99.9% | 2.56 | 100.0% | 5.08 | 99.7% | 3.77 | 98.9% |
| BS-OA-016 | 5.85 | 97.2% | 3 | 99.1% | 5.06 | 99.8% | 5.04 | 99.5% |
| BS-OA-027 | >16 | 35.5% | 9.96 | 80.1% | 7.79 | 68.9% | 6.63 | 91.6% |
| BS-OA-031 | >16 | 10.5% | >16 | 0.8% | >16 | 9.8% | >16 | 18.0% |
| BS-OA-032 | >16 | 5.2% | >16 | 14.1% | >16 | 32.5% | >16 | 26.3% |
| BS-OA-034 | >16 | 5.4% | >16 | −3.2% | >16 | 19.0% | >16 | 21.3% |
| BS-OA-035 | 5.34 | 98.5% | 2.56 | 98.9% | 5 | 98.5% | 3.72 | 98.6% |
| BS-OA-037 | >16 | 25.6% | 10.78 | 80.5% | 18.68 | 44.2% | 10.19 | 90.9% |
| BS-OA-042 | 5.99 | 95.2% | 2.84 | 99.2% | 4.78 | 100.0% | 3.63 | 97.9% |
| BS-OA-048 | >16 | −5.3% | >16 | −5.9% | >16 | 17.7% | >16 | 22.0% |
| BS-OA-052 | >16 | −11.3% | >16 | −12.7% | >16 | 25.4% | >16 | 29.5% |
| BS-OA-053 | >16 | −10.0% | >16 | 7.8% | >16 | 38.8% | >16 | 22.7% |
| BS-OA-059 | >16 | 0.0% | >16 | −7.4% | >16 | 34.1% | >16 | 35.2% |
| BS-OA-078 | 8.25 | 97.3% | 5.26 | 99.5% | 6.82 | 98.4% | 5.49 | 98.9% |
| BS-OA-105 | >16 | 28.4% | >16 | 29.2% | >16 | 18.4% | >16 | 5.0% |
| BS-OA-106 | >16 | 3.8% | >16 | 13.4% | >16 | −6.4% | >16 | −17.0% |
| BS-OA-108 | >16 | 22.7% | >16 | 13.1% | >16 | −8.2% | >16 | −15.6% |
| BS-OA-109 | >16 | 11.3% | >16 | 4.9% | >16 | −5.5% | >16 | −13.5% |
| BS-OA-110 | >16 | −6.3% | >16 | 2.9% | >16 | −11.4% | >16 | −20.1% |

The invention claimed is:
1. A 2-substituted oleanolic acid derivative of formula (I), or a pharmaceutically acceptable salt thereof,

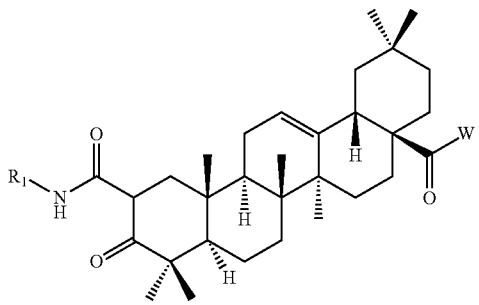

I wherein $R_1$ is selected from the group consisting of H, optionally substituted $C_1$-$C_{18}$ alkyl, optionally substituted $C_2$-$C_{18}$ alkenyl or alkynyl, optionally substituted $C_3$-$C_7$ cycloalkyl or cycloalkenyl, optionally substituted aryl, optionally substituted heterocyclyl or heteroaryl, each of which is optionally substituted with a substituent selected from the group consisting of halogen, nitro, cyano, amino, hydroxyl, thiol, carboxyl, $C_1$-$C_6$ alkylamino, bi($C_1$-$C_6$ alkyl)amino, $C_1$-$C_6$ alkoxy, and $C_1$-$C_6$ alkylthio, said $C_3$-$C_7$ cycloalkyl or cycloalkenyl, aryl, heterocyclyl or heteroaryl optionally further being substituted with $C_1$-$C_6$ alkyl, or $R_1$ being $C_1$-$C_6$ alkyl substituted with a group selected from said $C_3$-$C_7$ cycloalkyl or cycloalkenyl, aryl, heterocyclyl or heteroaryl; and wherein W is selected from the group consisting of hydroxyl, amino, $C_1$-$C_6$ alkylamino, bi($C_1$-$C_6$ alkyl)amino, $C_1$-$C_6$ alkoxy, and $C_1$-$C_6$ alkylthio.

2. The 2-substituted oleanolic acid derivative or a pharmaceutically acceptable salt thereof according to claim 1, wherein $R_1$ is $C_4$-$C_8$ alkyl, cycloalkyl-$C_1$-$C_6$ alkyl, heterocyclyl-$C_1$-$C_6$ alkyl, $C_1$-$C_6$ alkylamino-$C_1$-$C_6$ alkyl, bi($C_1$-$C_6$ alkyl)amino-$C_1$-$C_6$ alkyl, heteroaryl-$C_1$-$C_6$ alkyl, $C_1$-$C_6$ alkoxy-$C_1$-$C_6$ alkyl, said cycloalkyl, heterocyclyl and heteroaryl optionally being substituted with halogen, hydroxyl, $C_1$-$C_6$ alkoxy, $C_1$-$C_6$ alkyl, amino, $C_1$-$C_6$ alkylamino, or bi($C_1$-$C_6$ alkyl)amino.

3. The 2-substituted oleanolic acid derivative or a pharmaceutically acceptable salt thereof according to claim 1, wherein $R_1$ is $C_4$-$C_6$ alkyl, cycloalkyl-$C_1$-$C_4$ alkyl, heterocyclyl-$C_1$-$C_4$ alkyl, $C_1$-$C_6$ alkylamino-$C_1$-$C_4$ alkyl, bi($C_1$-$C_6$ alkyl)amino-$C_1$-$C_4$ alkyl, heteroaryl-$C_1$-$C_4$ alkyl, $C_1$-$C_6$ alkoxy-$C_1$-$C_4$ alkyl, said cycloalkyl, heterocyclyl and heteroaryl being optionally substituted with halogen, hydroxyl, $C_1$-$C_6$ alkoxy, $C_1$-$C_6$ alkyl, amino, $C_1$-$C_6$ alkylamino, or bi($C_1$-$C_6$ alkyl)amino.

4. The 2-substituted oleanolic acid derivative or a pharmaceutically acceptable salt thereof according to claim 1, wherein the heterocyclyl is a saturated heterocyclyl.

5. The 2-substituted oleanolic acid derivative or a pharmaceutically acceptable salt thereof according to claim 1, wherein the heterocyclyl comprises a nitrogen atom as a ring atom and as a connection point.

6. The 2-substituted oleanolic acid derivative or a pharmaceutically acceptable salt thereof according to claim 5, wherein the heterocyclyl is pyrrolidin-1-yl, piperidin-1-yl, piperazin-1-yl, 4-methylpiperazin-1-yl, morpholino, oxazolidinyl, imidazolidinyl, or isooxazolidinyl.

7. The 2-substituted oleanolic acid derivative or a pharmaceutically acceptable salt thereof according to claim 1, wherein W is hydroxyl or $C_1$-$C_6$ alkoxy.

8. The 2-substituted oleanolic acid derivative or a pharmaceutically acceptable salt thereof according to claim 1, wherein the heteroaryl is pyridyl, furanyl, thienyl, pyrrolyl, pyranyl, or imidazolyl.

9. The 2-substituted oleanolic acid derivative or a pharmaceutically acceptable salt thereof according to claim 1, which is selected from the group consisting of the following compounds:

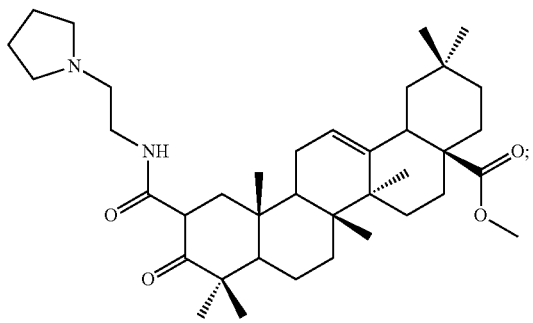

Methyl 1-oxo-2-(N-(pyrrolidinylethyl))aminocarbonyl oleanolate

BS-OA-005

BS-OA-012

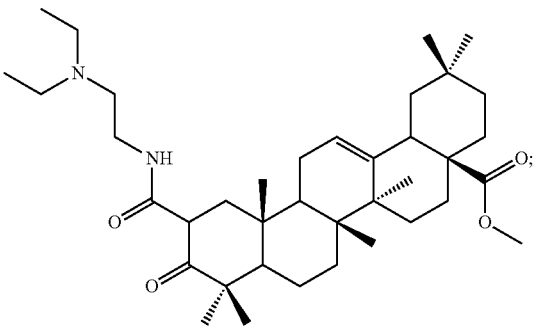

Methyl 1-oxo-2-(N-(diethylaminoethyl))aminocarbonyl oleanolate

BS-OA-016

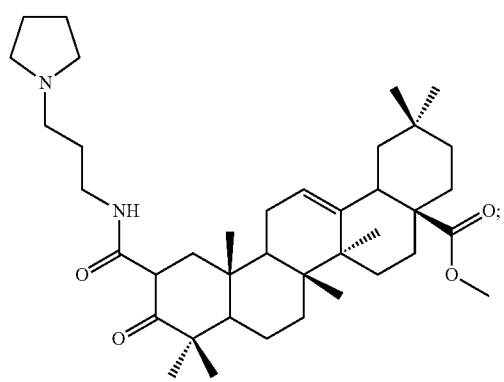

Methyl 1-oxo-2-(N-(pyrrolidinylpropyl))aminocarbonyl oleanolate

-continued

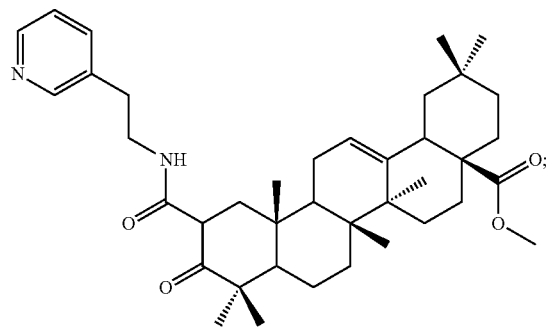

BS-OA-027

Methyl 1-oxo-2-(N-(3-pyridylethyl))aminocarbonyl oleanolate

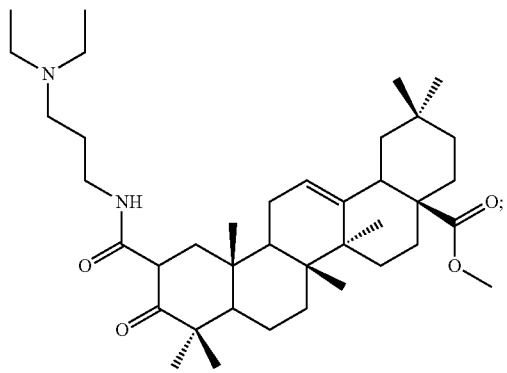

BS-OA-035

Methyl 1-oxo-2-(N-(diethylaminopropyl))aminocarbonyl oleanolate

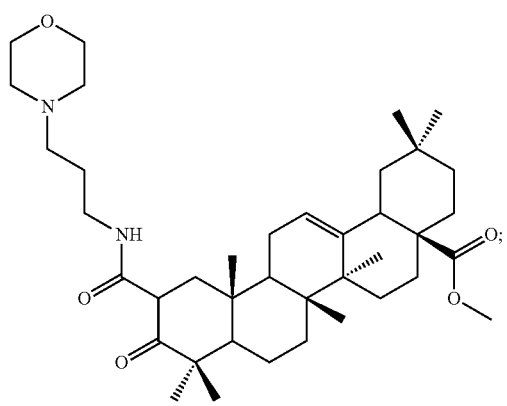

BS-OA-037

Methyl 1-oxo-2-(N-(morpholinypropyl))aminocarbonyl oleanolate

-continued

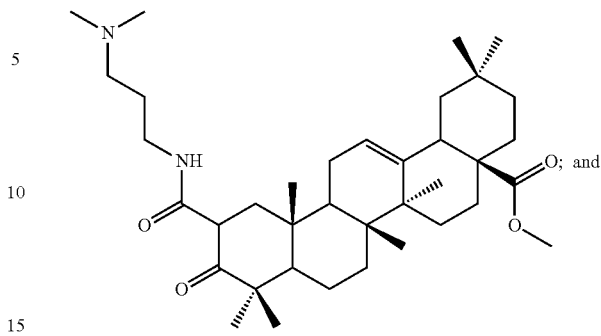

BS-OA-042

Methyl 1-oxo-2-(N-(dimethylaminopropyl))aminocarbonyl oleanolate

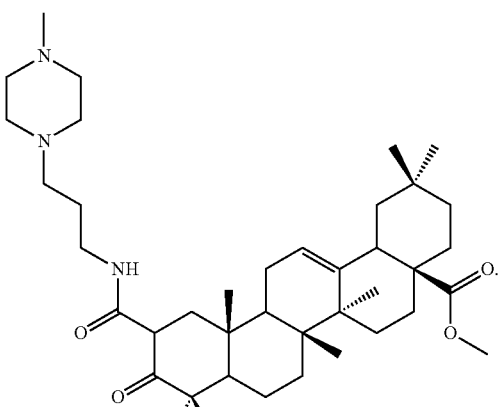

BS-OA-078

Methyl 1-oxo-2-(N-(N-methylpiperazinylpropyl))aminocarbonyl oleanolate

10. A process for preparing the compound of formula (I), wherein oleanolic acid (OA)

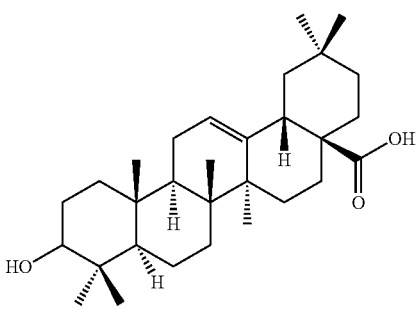

(OA)

is subjected to oxidation with pyridinium chlorochromate to produce a ketone intermediate of oleanolic acid (OA-1)

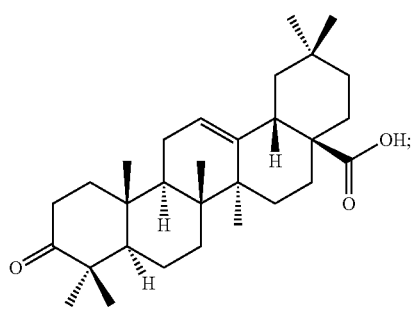
(OA-1)

said intermediate is subjected to methyl esterification with iodomethane to produce a methyl esterified (ketone) intermediate of oleanolic acid (OA-2)

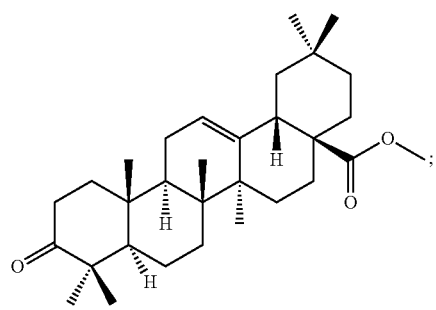
(OA-2)

said intermediate is reacted with Stile's Reagent and introduces a methoxycarbonyl group to the ortho-position of the ketone carbonyl to produce a diester intermediate of oleanolic acid (OA-3)

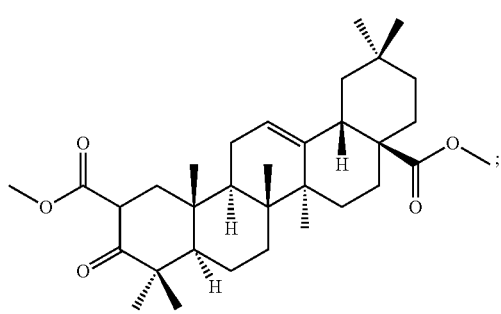
(OA-3)

said diester intermediate is hydrolyzed by NaOH to produce a monocarboxyl intermediate of oleanolic acid (OA-4)

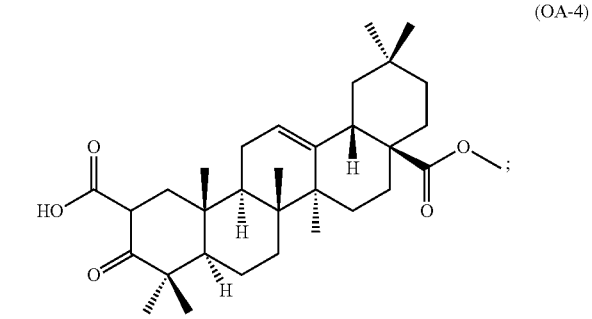
(OA-4)

or, wherein the introduction of the methoxycarbonyl group and the hydrolysis are completed in a one-pot reaction to produce the monocarboxyl intermediate of oleanolic acid (OA-4);

said monocarboxyl intermediate is subjected to an amido bond formation reaction with an organic amine, $R_1NH_2$, to produce the 2-substituted oleanolic acid derivative (I)

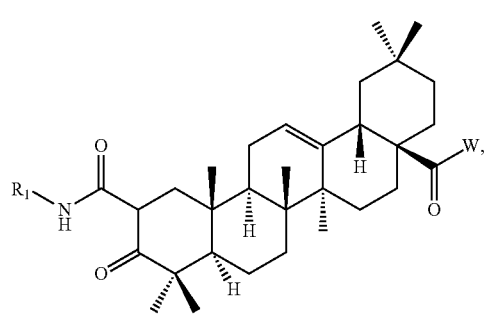
(I)

wherein $R_1$ is as defined in formula (I) of claim 1, and wherein W is methoxy.

11. A pharmaceutical composition, comprising the 2-substituted oleanolic acid derivative or a pharmaceutically acceptable salt thereof according to claim 1 and optionally a pharmaceutically acceptable excipient.

12. A method of treating a tumor in a subject in need thereof, comprising administering to the subject in an effective amount of the 2-substituted oleanolic acid derivative or a pharmaceutically acceptable salt thereof according to claim 1, wherein said treating refers to causing regression of the tumor.

13. The method of claim 12, wherein the tumor is selected from leukemia, multiple myeloma, lymphoma, liver cancer, gastric cancer, breast cancer, cholangiocellular carcinoma, pancreatic cancer, lung cancer, colorectal cancer, osteosarcoma, human cervical cancer, glioma, nasopharyngeal carcinoma, laryngeal carcinoma, esophageal cancer, middle ear tumor, melanoma and prostate cancer.

* * * * *